United States Patent
Qiu et al.

(10) Patent No.: US 12,162,933 B2
(45) Date of Patent: Dec. 10, 2024

(54) MODIFIED-IgG ANTIBODIES THAT BIND TRANSFORMING GROWTH FACTOR-β1 WITH HIGH AFFINITY, AVIDITY AND SPECIFICITY

(71) Applicant: Genzyme Corporation, Cambridge, MA (US)

(72) Inventors: Huawei Qiu, Framingham, MA (US); Julie Bird, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/492,150

(22) Filed: Oct. 23, 2023

(65) Prior Publication Data

US 2024/0117028 A1 Apr. 11, 2024

Related U.S. Application Data

(62) Division of application No. 17/717,967, filed on Apr. 11, 2022, now Pat. No. 11,834,495, which is a division of application No. 15/555,500, filed as application No. PCT/US2016/020780 on Mar. 3, 2016, now Pat. No. 11,325,970.

(60) Provisional application No. 62/128,149, filed on Mar. 4, 2015.

(51) Int. Cl.
| | | |
|---|---|---|
| *A61K 39/395* | (2006.01) | |
| *A61P 19/08* | (2006.01) | |
| *C07K 16/22* | (2006.01) | |
| *C12N 15/11* | (2006.01) | |

(52) U.S. Cl.
CPC .......... *C07K 16/22* (2013.01); *A61K 39/3955* (2013.01); *C12N 15/11* (2013.01); *C07K 2317/14* (2013.01); *C07K 2317/21* (2013.01); *C07K 2317/34* (2013.01); *C07K 2317/52* (2013.01); *C07K 2317/522* (2013.01); *C07K 2317/53* (2013.01); *C07K 2317/55* (2013.01); *C07K 2317/56* (2013.01); *C07K 2317/567* (2013.01); *C07K 2317/622* (2013.01); *C07K 2317/76* (2013.01); *C07K 2317/92* (2013.01); *C07K 2317/94* (2013.01)

(58) Field of Classification Search
CPC .. A61K 39/395; A61K 39/3955; C07K 16/22; A61P 19/08
See application file for complete search history.

(56) References Cited

U.S. PATENT DOCUMENTS

| | | |
|---|---|---|
| 5,616,561 A | 4/1997 | Barcellos-Hoff |
| 6,492,497 B1 * | 12/2002 | Thompson .............. A61P 35/00 424/156.1 |
| 7,151,169 B2 | 12/2006 | Thompson et al. |
| 7,619,069 B2 | 11/2009 | Davies et al. |
| 8,048,421 B2 | 11/2011 | Kai et al. |
| 8,632,774 B2 | 1/2014 | Misher et al. |
| 10,508,146 B2 | 12/2019 | Qiu et al. |
| 11,325,970 B2 | 5/2022 | Qiu et al. |
| 11,325,971 B2 | 5/2022 | Qiu et al. |
| 2002/0099179 A1 | 7/2002 | Jolliffe et al. |
| 2008/0050375 A1 | 2/2008 | Davies et al. |
| 2010/0174053 A1 | 7/2010 | Johnson et al. |
| 2014/0072581 A1 | 3/2014 | Dixit et al. |
| 2018/0044412 A1 | 2/2018 | Qiu et al. |
| 2018/0222970 A1 | 8/2018 | Qiu et al. |
| 2020/0131258 A1 | 4/2020 | Qiu et al. |
| 2022/0315649 A1 | 10/2022 | Qiu et al. |
| 2022/0363740 A1 | 11/2022 | Qiu et al. |

FOREIGN PATENT DOCUMENTS

| | | |
|---|---|---|
| EP | 1486560 | 12/2004 |
| WO | WO 00/66631 A1 | 11/2000 |
| WO | WO 2004/098637 A1 | 11/2004 |
| WO | WO 2005/097832 A2 | 10/2005 |
| WO | WO 2006/036729 A3 | 4/2006 |
| WO | WO 2006/116002 A2 | 11/2006 |
| WO | WO 2007/109254 A1 | 2/2007 |
| WO | WO 2007/076391 A1 | 7/2007 |
| WO | WO 2008/060371 A1 | 5/2008 |
| WO | WO 2012/088461 A2 | 6/2012 |
| WO | WO 2012/135345 A1 | 10/2012 |
| WO | WO 2012/167143 A1 | 12/2012 |
| WO | WO 2014/164709 A2 | 10/2014 |

OTHER PUBLICATIONS

Aalberse et al., "IgG4 breaking the rules," Immunol. (2002) 105:9-19.
Alekperov, "Treatment of systemic scleroderma," *Russ. Open Med. J.* (2002) No. 22.
Armour et al., "Recombinant human IgG molecules lacking Fcgamma receptor I binding and monocyte triggering activities," *Eur J Immunol.* (1999) 29(8):2613-24.
Beck et al., "Strategies and challenges for the next generation of therapeutic antibodies," *Nature Reviews, Immunol.* (2010) 10:345-52.

(Continued)

*Primary Examiner* — Xiaozhen Xie

(74) *Attorney, Agent, or Firm* — Steptoe LLP; Z. Ying Li; Mauricio Alvarez

(57) ABSTRACT

A modified IgG antibody binds and neutralizes TGFβ1 selectively and with high affinity and avidity. The modified IgG antibody comprises four polypeptide chains and may comprise modifications to the elbow regions of the polypeptide chains. The modified IgG antibody may comprise the same VH and VL domains or CDR regions as metelimumab. The modified IgG anti-body is useful in therapeutic and diagnostic applications.

9 Claims, 17 Drawing Sheets

Specification includes a Sequence Listing.

(56) References Cited

OTHER PUBLICATIONS

Berry et al., "Substitution of cysteine for selenocysteine in type I iodothyronine deiodinase reduces the catalytic efficiency of the protein but enhances its translation," *Endocrinology* (1992) 131(4):1848-52.

Bird et al., "Single-Chain Antigen-Binding Proteins," *Science* (1988) 242:423-26.

Border et al., "Suppression of experimental glomerulonephritis by antiserum against transforming growth factor β1," *Nature* (1990) 346:371-74.

Borsi et al., "Selective Targeting of Tumoral Vasculature: Comparison of Different Formats of an Antibody (L19) to the ED-B Domain of Fibronectin," *Int. J. Cancer.* (2002) 102:75-85.

Bujak et al., "Reformatting of scFv antibodies into the scFv-Fc format and their downstream purification," *Methods Mol Biol.* (2014) 1131:315-34.

Chen et al., "Enhancement and destruction of antibody function by somatic mutation: unequal occurrence is controlled by V gene combinatorial associations," *EMBO J.* (1995) 14(12):2784-94.

Chiu et al., "Antibody Structure and Function: The Basis for Engineering Therapeutics," *Antibodies* (2019) 8(4):55.

Colman, "Effects of amino acid sequence changes on antibody-antigen interactions," Res Immunol. (1994) 145(1):33-36.

Correa et al., "Structure of a human IgA1 Fab fragment at 1.55   Å resolution: potential effect of the constant domains on antigen-affinity modulation," *Acta Crystallogr D Biol Crystallogr.* (2013) 69(3):388-97.

Waterhouse et al: "Jalview Version 2—a multiple sequence alignment editor and analysis workbench," *Bioinformatics* (2009) 1189-91.

Datta-Mannan et al., "Humanized IgG1 variants with differential binding properties to the neonatal Fc receptor: relationship to pharmacokinetics in mice and primates," *Drug Metab Dispos.* (2007) 35:86-94.

Dondelinger et al., "Understanding the Significance and Implications of Antibody Numbering and Antigen-Binding Surface/Residue Definition", (2018) *Front Immunol.* 9:2278.

Fernandez-Quintero et al., "Suprisingly Fast Interface and Elbow Angle Dynamics of Antigen-Binding Fragments," *Front. Mol. Biosci.* (2020) 7:609088.

Gao et al., "Construction of Pichia pastoris expression vector for production of scFv-Fc fusion antibody against 40,000 adipocyte-specific plasma membrane protein," *Chin. J. Prev. Vet.* (2007) 27(3)376-86.

Gasser et al., "Antibody production with yeasts and filamentous fungi: on the road to large scale?" *Biotechnol Lett.* (2007) 29(2):201-12.

Giri et al., "Effect of antibody to transforming growth factor β on bleomycin induced accumulation of lung collagen in mice," *Thorax* (1993) 48:959-66.

Grütter et al., "A cytokine-neutralizing antibody as a structural mimetic of 2 receptor interactions," *Proc Natl Acad Sci USA.* (2008) 105(51):20251-6. doi: 10.1073/pnas.0807200106.

Harding et al., "The immunogenicity of humanized and fully human antibodies," *mAbs* (2010) 2(3):256-65.

Hieter et al., "Cloned human and mouse kappa immunoglobulin constant and J region genes conserve homology in functional segments," *Cell, Cell Press* (1980) 22(1):197-207.

Hinton et al., "Engineered Human IgG Antibodies with Longer Serum Half-lives in Primates," *Chem.* (2004) 279(8):6213-16.

Holliger et al., "Engineered antibody fragments and the rise of single domains," (2005) Nat Biotechnol. 23:1126-36.

Holmes et al., "Structural Consequences of Humanizing an Antibody," *J Immunol.* (1997) 158(5):2192-2201.

Huston et al., "Protein engineering of antibody binding sites: Recovery of specific activity in an anti-digoxin single-chain Fv analogue produced in *Escherichia coli*," *Proc Natl Acad Sci USA.* (1988) 85(16):5879-83.

Idusogie et al., "Engineered Antibodies with Increased Activity to Recruit Complement," *J Immunol.* (2001) 166(4):2571-75.

Idusogie et al., "Mapping of the C1q Binding Site on Rituxan, a Chimeric Antibody with a Human IgG1 Fc," *J Immunol.* (2000) 164(8):4178-84.

Ishii-Watabe et al., "Molecular Design of Therapeutic Monoclonal Antibodies," PDA J Pharm Sci Technol. (2014) 74(1):4-11.

Katsumoto et al., "The Pathogenesis of Systemic Sclerosis," *Annual Review Of Pathology: Mechanisms of Disease* (2011) 6(1):509-37.

Knappik et al., "Fully synthetic human combinatorial antibody libraries (HuCAL) based on modular consensus frameworks and CDRs randomized with trinucleotides," *J Mol Biol.* (2000) 296(1):57-86.

Kussie et al., "A single engineered amino acid substitution changes antibody fine specificity," J Immunol. (1994) 152(1):146-52.

Labrijn et al., "Therapeutic IgG4 antibodies engage in Fab-arm exchange with endogenous human IgG4 in vivo," *Nature Biotechnol.* (2009) 27:767-71.

Landolfi et al., "The integrity of the ball-and-socket joint between V and C domains is essential for complete activity of a humanized antibody." *Am. J. Immunol.* (2001) 166(3):1748-54.

Lazar et al., "Engineered antibody Fc variants with enhanced effector function," *Proc. Natl Acad. Sci. USA.* (2006) 103:4005-10.

Lesk et al., "Elbow motion in the immunoglobulins involves a molecular ball-and-socket joint," *Nature* (1988) 335:188-190.

Logan et al., "Effects of transforming growth factor beta 1 on scar production in the injured central nervous system of the rat," *Eur J Neurosci.* (1994) 6:355-63.

Olafsen et al., "Antibody Vectors for Imaging," *Semin Nucl Med.* (2010) 40:167-81.

Peters et al., "Engineering an Improved IgG4 Molecule with Reduced Disulfide Bond Heterogeneity and Increased Fab Domain Thermal Stability," *J. Biol. Chem.* (2012) 287(29):24525-33.

Ponomarenko et al., "Role of [kappa]->[lambda] light-chain constant-domain switch in the structure and functionality of A17 reactibody," *Acta. Crystallogr. B. Struct.* (2014) 341(3):708-19.

Powers et al., "Expression of single-chain Fv-Fc fusions in Pichia pastoris," *J Immunol Methods.* (2001) 251:123-35.

Richards et al., "Optimization of antibody binding to FcgammaRIIa enhances macrophage phagocytosis of tumor cells," *Mol Cancer Ther* (2008) 7(8) 2517-27.

Rispens et al., "Dynamics of inter-heavy chain interactions in human immunoglobulin G (IgG) subclasses studied by kinetic Fab arm exchange," *J Biol Chem.* (2014) 289(9):6098-6109.

Rudikoff et al., "Single amino acid substitution altering antigen-binding specificity," *Proc Natl Acad Sci USA.* (1982) 79(6):1979-83.

Ryan et al., "Antibody targeting of B-cell maturation antigen on malignant plasma cells," Mol Cancer Ther. (2007) 6(11):3009-18.

Sela-Culang et al., "The structural basis of antibody-antigen recognition," *Front Immunol.* (2013) 4:302.

Shah et al., "Neutralisation of TGF-beta 1 and TGF-beta 2 or exogenous addition of TGF-beta 3 to cutaneous rat wounds reduces scarring," *J. Cell Science.* (1995) 108:985-1002.

Shah et al., "Control of scarring in adult wounds by neutralising antibody to transforming growth factor β," *Lancet* (1992) 339(8787):213-4.

Shah et al., "Neutralising antibody to TGF-β1,2 reduces cutaneous scarring in adult rodents," *J Cell Sci.* (1994) 107(5):1137-57.

Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.* (2001) 276:6591-6604.

Stanfield et al., "Antibody Elbow Angles are Influenced by their Light Chain Class," *J. Mol. Biol.* (2006) 357(5):1566-74.

Steurer et al., "Ex vivo coating of islet cell allografts with murine CTLA4/Fc promotes graft tolerance," *J. Immunol.* 155:1165-74 (1995).

Strohl, "Optimization of Fc-mediated effector functions of monoclonal antibodies," *Curr Opin Biotechnol.* (2009) 20:685-91.

Torres et al., "The immunoglobulin constant region contributes to affinity and specificity," *Trends Immunol.* (2008) 29(2):91-97.

Vaccaro et al., "Engineering the Fc region of immunoglobulin G to modulate in vivo antibody levels," *Nat Biotechnol.* (2005) 23:1283-8.

(56) References Cited

OTHER PUBLICATIONS

Wahl et al., "Reversal of acute and chronic synovial inflammation by anti-transforming growth factor beta," *Exp. Medicine*. (1993) 177:225-30.
Yusakul et al., "Effect of linker length between variable domains of single chain variable fragment antibody against daidzin on its reactivity," *Biosci Biotechnol Biochem*. (2016) 80(7):1306-12.
Zhang et al., "Determination of Fab-Hinge Disulfide Connectivity in Structural Isoforms of a Recombinant Human Immunoglobulin G2 Antibody," *Anal. Chem*. (2010) 82:1090-99.
Zhou et al., "AmphireguUn, an Epidermal Growth Factor Receptor ligand, Plays an Essential Role in the Pathogenesis of Transforming Growth Factor-beta-induced Pulmonary Fibrosis," J. Biol. Chem. (2012) 287(50):41991-2000.

\* cited by examiner

MODIFIED-IgG ANTIBODIES THAT BIND TRANSFORMING GROWTH FACTOR-β1 WITH HIGH AFFINITY, AVIDITY AND SPECIFICITY

RELATED APPLICATIONS

This patent application is a divisional of U.S. patent application Ser. No. 17/717,967, filed Apr. 11, 2022, now U.S. Pat. No. 11,834,495, which claims the benefit of the divisional of U.S. patent application Ser. No. 15/555,500, filed Sep. 2, 2017, now U.S. Pat. No. 11,325,970, which claims the benefit of National Stage under 35 U.S.C. § 371 of International Application No. PCT/US2016/020780, filed Mar. 3, 2016, which claims the benefit of U.S. Provisional Patent Application 62/128,149, filed Mar. 4, 2015. The disclosures of both of the International Application and the Provisional Application are incorporated herein by reference in their entirety.

REFERENCE TO ELECTRONIC SEQUENCE LISTING

The application contains a Sequence Listing which has been submitted electronically in .XML format and is hereby incorporated by reference in its entirety. Said .XML copy, created on Oct. 17, 2023, is named "022548.D2016.xml" and is 64,955 bytes in size. The sequence listing contained in this .XML file is part of the specification and is hereby incorporated by reference herein in its entirety.

BACKGROUND OF THE INVENTION

Field of the Invention

Modified-IgG antibodies, each comprising a first, a second, a third and a fourth polypeptide chain, which exhibit high affinity and avidity to Transforming Growth Factor-β1 (TGFβ1) but not to TGFβ2 or TGFβ3. Compositions comprising the modified-IgG antibodies and methods of using the same for treatment of diseases involving TGFβ1 activity are provided.

Many severe diseases are linked to malfunctions of the TGFβ-induced signaling pathway. For instance, an increased tissue level of TGFβ is believed to be a factor in the development of idiopathic pulmonary fibrosis and myocardial fibrosis. Furthermore, high local tissue levels of TGFβ may allow the maintenance and progression of some types of cancer cells. Down-regulation of TGFβ signaling therefore may reduce the viability of such tumor cells.

TGFβ isoforms are ~25 kDa homodimeric molecules with a similar structural framework in which two monomers are covalently linked via a disulfide bridge. The mammalian isoforms share a sequence identity of 70-82%, but have non-overlapping activities in vascular development and the regulation of immune cell function. Three TGFβ isoforms have been reported in humans: TGFβ1, TGFβ2, and TGFβ3 (Swiss Prot accession numbers P01137, P08112, and P10600, respectively). TGFβ1 and TGFβ3 trigger a cellular signaling cascade upon binding to the extracellular domains of two transmembrane receptors, known as TGFβ receptor types I and II. TGFβ2 may bind to TGFβ receptor types I and II, as well as TGFβ receptor type III.

Antibodies that can bind human TGFβ1, TGFβ2, and TGFβ3 have been tested for clinical use. For instance, Grütter et al. disclosed GC1008, a human IgG4 monoclonal antibody (Mab; i.e., GC1008) in clinical development for treating malignancy and fibrotic diseases. *Proc. Nat'l Acad. Sci. USA* 105(51): 20251-56 (2008). GC1008 is a "pan-specific" TGFβ neutralizing antibody, because it can neutralize all three human TGFβ isoforms. Antibodies that selectively neutralize TGFβ1 are disclosed, for example, in U.S. Pat. Nos. 6,492,497 and 7,151,169, which are incorporated by reference into this disclosure. Metelimumab, also known as CAT192 (IgG4), is a human IgG4 monoclonal antibody that selectively neutralizes TGF-β1. See e.g., U.S. Pat. No. 6,492,497. Metelimumab was tested for the treatment of diffuse cutaneous systemic sclerosis, also known as scleroderma, but demonstrated insufficient efficacy.

BRIEF SUMMARY OF THE INVENTION

The present disclosure provides TGFβ1-binding modified-IgG antibodies that are capable of selectively binding and neutralizing human TGFβ1. The disclosed modified-IgG antibodies are derived from metelimumab. The VH and VL domains of the modified-IgG antibodies exhibit a TGFβ1-binding affinity and avidity and TGFβ1 neutralizing capability similar to those of metelimumab. In many cases, the disclosed antibodies offer improved affinity, avidity and neutralization capacity over metelimumab. In one embodiment, the modified-IgG antibodies contain two polypeptide chains each comprising a VL domain linked to a CL domain, and two polypeptide chains each comprising a VH domain linked to a CH1 domain, a hinge and a Fc region.

The modified-IgG antibodies of the present invention comprise a variable domain that is capable of binding TGFβ1. In another embodiment, the disclosed modified-IgG antibodies comprise a binding protein which exhibits a Kd for human TGFβ1 at least about 50% lower than the Kd of the same binding protein for human TGFβ2, as measured by surface plasmon resonance.

In another embodiment, the present invention is directed to an isolated binding protein comprising a variable domain that is capable of binding TGFβ1, wherein the binding protein exhibits a Kd for human TGFβ1 at least about 50% lower than the Kd of the same binding protein for human TGFβ3, as measured by surface plasmon resonance.

In a further embodiment, the present invention is directed to an isolated binding protein comprising a variable domain that is capable of binding TGFβ1, wherein the binding protein exhibits a Kd for human TGFβ1 at least about 50% lower than the Kd of the same binding protein for human TGFβ2, and at least about 50% lower than the Kd of the same binding protein for human TGFβ3, as measured by surface plasmon resonance.

In a further embodiment, the present invention is directed to an isolated binding protein that binds TGFβ1, wherein the binding protein comprises a first polypeptide chain, a second polypeptide chain, a third polypeptide chain and a fourth polypeptide chain. In one aspect, the first and second polypeptide chains have the formula of, from N-terminal to C-terminal:

(VL domain)-(linker1)$_m$-(CL domain), wherein the VL domain comprises a variable light complementarity determining region 1 (LCDR1), a variable light complementarity determining region 2 (LCDR2), and a variable light complementarity determining region 3 (LCDR3), and wherein m is 1, and wherein the linker1 comprises a peptide having the sequence of Leucine-Glutamic acid-Isoleucine-Lysine-$X_p$-$Y_q$-$Z_r$-Arginine-Threonine-Valine-Alanine, X, Y and Z being independently an amino acid selected from the group consisting of Serine, Glycine, Alanine, Valine, Leucine, Isoleucine, and Threonine, and each of p, q and r being independently an integer from 0 to 5. In another aspect, the third and fourth polypeptide chains have the formula of, from N-terminal to C-terminal:

(VH domain)-(linker2)$_n$-(CH1 domain)-(hinge)$_s$-
(Fc region), wherein the VH domain comprises a variable heavy complementarity determining region 1 (HCDR1), a variable heavy complementarity determining region 2 (HCDR2), and a variable heavy complementarity determining region 3 (HCDR3); and wherein n is 0 or 1 and s is 0 or 1. In another aspect, linker2 may contain a peptide having the sequence of Threonine-Valine-Serine-A$_d$-B$_e$-C$_f$-Serine-Alanine-Serine-Threonine, A, B and C being independently an amino acid selected from the group consisting of Serine, Glycine, Alanine, Valine, Leucine, Isoleucine, and Threonine, and each of d, e and f being independently an integer from 0 to 5.

In one aspect, linker2 may contain a sequence selected from the group consisting of SEQ ID No. 45, SEQ ID No. 46, SEQ ID No. 47, and SEQ ID No. 48.

In one aspect, the HCDR1 may have the amino acid sequence of SEQ ID No. 7, The HCDR2 may have the amino acid sequence of SEQ ID No. 8, and the HCDR3 may have the amino acid sequence of SEQ ID No. 9, SEQ ID No. 10, SEQ ID No. 11, or SEQ ID No. 15.

The framework regions of the VH domain may be selected from a variable heavy germline sequence. The VH domain may be selected, for example, from the human VH domain sequences set forth in SEQ ID No. 1 or SEQ ID No. 2, or a variant thereof having modifications of up to five amino acids.

The VL domain of the disclosed binding protein may comprise a variable light complementarity determining region 1 (LCDR1), a variable light complementarity determining region 2 (LCDR2), and a variable light complementarity determining region 3 (LCDR3). In one aspect, the LCDR1 may have the amino acid sequence of SEQ ID No. 12, the LCDR2 may have the amino acid sequence of SEQ ID No. 13, and the LCDR3 may have the amino acid sequence of SEQ ID No. 14.

The framework regions of the VL domain may be selected from a variable lambda or kappa germline sequence. The VL domain may be selected, for example, from the human Vκ domain sequences set forth in SEQ ID No. 3 or SEQ ID No. 4, or a variant thereof having modifications of up to four amino acids. In one embodiment, each polypeptide of the dimer may comprise the VH domain set forth in SEQ ID NO: 1 and the Vκ domain set forth in SEQ ID No. 3, which are the VH and VL domains present in metelimumab, respectively.

In another embodiment, the Fc region is connected to the CH1 domain by a hinge. The hinge may comprise amino acid sequences derived from a human IgG1 or IgG4 hinge region. For example, the hinge may comprise the amino acid sequence PKSCDKTHTCPPCPAPELLGGP (SEQ ID No. 5), or a variant thereof having up to five amino acid modifications. In one embodiment, the hinge length may vary from 1-15 amino acids.

In another embodiment, site-directed mutagenesis is performed on CAT192 Fab elbow regions to improve TGFβ1 binding affinity. One to five amino acids (G, GG, GGS, GGGS (SEQ ID NO: 62) and GGGGS (SEQ ID NO: 63)) are inserted to the light chain elbow region to increase the flexibility of the hinge that may be required to present a functional binding paratope from the two chains. Conditioned media from an Expi293 transfection show good expression and significant improvement in binding to TGFβ1 by Octet. The mutants are purified by Ni-NTA and high TGFβ binding affinities are confirmed using Biacore. The CAT192 mutants with 1 to five amino acids inserted into the LC elbow region re-gain the high affinity binding of scFv to TGFβ1. These engineered elbow insertion mutants also retain isoform-selectivity and may serve as TGFβ1 specific antagonists.

In another aspect, the VH domain may contain a variable heavy complementarity determining region 1 (HCDR1) having the amino acid sequence of SEQ ID No. 7, a variable heavy complementarity determining region 2 (HCDR2) having the amino acid sequence of SEQ ID No. 8, and a variable heavy complementarity determining region 3 (HCDR3) having the amino acid sequence selected from the group consisting of SEQ ID No. 9, SEQ ID No. 10, SEQ ID No. 11, and SEQ ID No. 15.

In another aspect, the VL domain may contain a variable light complementarity determining region 1 (LCDR1) having the amino acid sequence of SEQ ID No. 12, a variable light complementarity determining region 2 (LCDR2) having the amino acid sequence of SEQ ID No. 13, and a variable light complementarity determining region 3 (LCDR3) having the amino acid sequence of SEQ ID No. 14.

In another aspect, linker1 may contain a peptide having the sequence of Leucine-Glutamic acid-Isoleucine-Lysine-X$_p$-Y$_q$-Z$_r$-Arginine-Threonine-Valine-Alanine, wherein X, Y and Z is independently an amino acid selected from the group consisting of Serine, Glycine, Alanine, Valine, Leucine, Isoleucine, and Threonine, and each of p, q and r is independently an integer from 0 to 5. In another aspect, each of X, Y and Z is preferably Serine and Glycine. In another aspect, each of p, q and r is 1. In another aspect, p is 0 and each of q and r is 1. In another aspect, p is 1 and each of q and r is 0. In another aspect, p is 2 and each of q and r is 1. In another aspect, p is 1 and each of q and r is 2.

In one embodiment, linker1 may contain a sequence selected from the group consisting of SEQ ID No. 22, SEQ ID No. 23, SEQ ID No. 24, SEQ ID No. 25, and SEQ ID No. 26, each of which is a mutated form derived from SEQ ID No. 21. In another embodiment, the first polypeptide chain contains a sequence selected from the group consisting of SEQ ID No. 39, SEQ ID No. 40, and SEQ ID No. 41, each of which is a mutated form derived from the light chain of CAT192 IgG1 (SEQ ID No. 38).

In another aspect, linker1 and linker2 may be each independently as described for linker1 above. In this aspect, linker2 may contain a peptide having the sequence of Leucine-Glutamic acid-Isoleucine-Lysine-A$_d$-B$_e$-C$_f$-Arginine-Threonine-Valine-Alanine, wherein A, B and C is independently an amino acid selected from the group consisting of Serine, Glycine, Alanine, Valine, Leucine, Isoleucine, and Threonine, and each of d, e and f is independently an integer from 0 to 5. In another aspect, each of A, B and C is preferably Serine and Glycine. In another aspect, each of d, e and f is 1. In another aspect, d is 0 and each of e and f is 1. In another aspect, d is 1 and each of e and f is 0. In another aspect, d is 2 and each of e and f is 1. In another aspect, d is 1 and each of e and f is 2.

In another embodiment, the linker2 may contain a sequence selected from the group consisting SEQ ID No. 22, SEQ ID No. 23, SEQ ID No. 24, SEQ ID No. 25, and SEQ ID No. 26, each of which is a mutated form derived from SEQ ID No. 21. In another embodiment, the first polypeptide chain contains a sequence selected from the group consisting of SEQ ID No. 39, SEQ ID No. 40, and SEQ ID No. 41, each of which is a mutated form derived from the light chain of CAT192 IgG1 (SEQ ID No. 38).

In another embodiment, the disclosed TGFβ1-binding Fab or IgG molecules selectively binds TGFβ1, but does not bind TGFβ2 or TGFβ3 to a significant extent.

In another embodiment, an isolated polynucleotide is disclosed which may comprise a nucleotide sequence encoding the modified IgG antibodies disclosed herein. The isolated polynucleotide may be a cDNA, a recombinant DNA or a synthetic DNA. A host cell may comprise the isolated nucleic acid. The host cell may be a human cell, such as a Human Embryonic Kidney 293 (HEK293) cell and cell lines derived therefrom, or it may be a Chinese Hamster Ovary (CHO) cell. A method of making the modified IgG antibodies may include culturing the host cell under suitable conditions to produce the modified IgG antibodies. The modified IgG antibodies may be purified. The degree of purity may be 90%, 95%, 99%, 99.5% or more.

In certain embodiments, the modified IgG antibodies of the present invention may be an element of a composition. The composition may be a pharmaceutical composition. The pharmaceutical composition may comprise a therapeutically effective amount of the modified IgG antibodies. The composition may further comprise one or more biologically active components, excipients, or diluents.

Also provided is a method of treating a disease or condition resulting directly or indirectly from TGFβ1 activity in a human comprising administering a pharmaceutical composition comprising a therapeutically effective amount of the modified IgG antibodies. The disease or condition may be selected from the group consisting of a fibrotic disease, cancer, or an immune-mediated disease, e.g., diffuse cutaneous systemic sclerosis, bone remodeling disease, kidney disease and/or a combination thereof. The modified IgG antibodies may be used in the manufacture of a medicament for treatment of a disease or disorder selected from the group consisting of a fibrotic disease, cancer, or an immune-mediated disease, e.g., diffuse cutaneous systemic sclerosis, bone remodeling disease, kidney disease and/or a combination thereof. The treatment of the disease or disorder may comprise neutralizing TGFβ1 or inhibiting TGFβ1 signaling. The treatment of the disease or disorder may comprise inhibiting TGFβ1-mediated fibronectin production, vascular endothelial growth factor (VEGF) production, epithelial cell proliferation, endothelial cell proliferation, smooth muscle cell proliferation, and/or immunosuppression. The treatment of the disease or disorder may comprise increasing natural killer cell activity.

BRIEF DESCRIPTION OF THE SEVERAL VIEWS OF THE DRAWING(S)

The drawings presented herein are for purpose of illustration and are not to be used to limit the scope of the present invention.

DETAILED DESCRIPTION OF THE INVENTION

Figure 1:
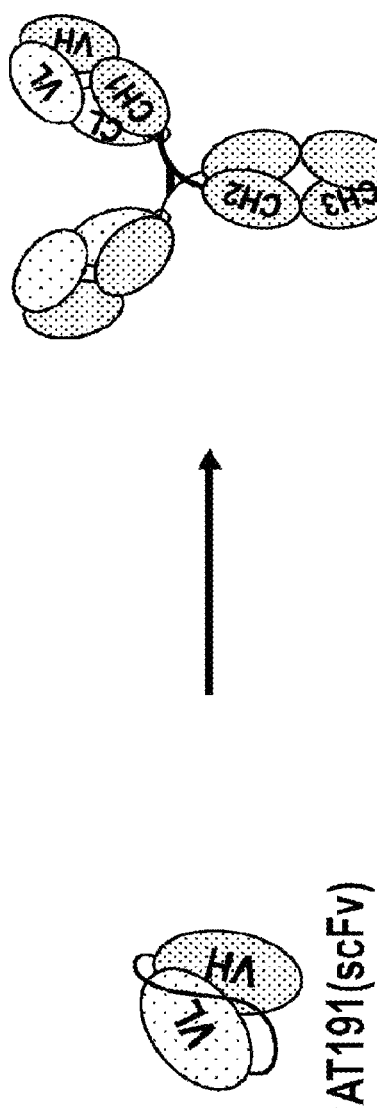
FIG. 1 depicts the results of a Biacore TGFβ1 binding assay which showed the loss of affinity when the scFv (CAT191) was converted into a full length IgG4 (CAT192) molecule.
Figure 1:
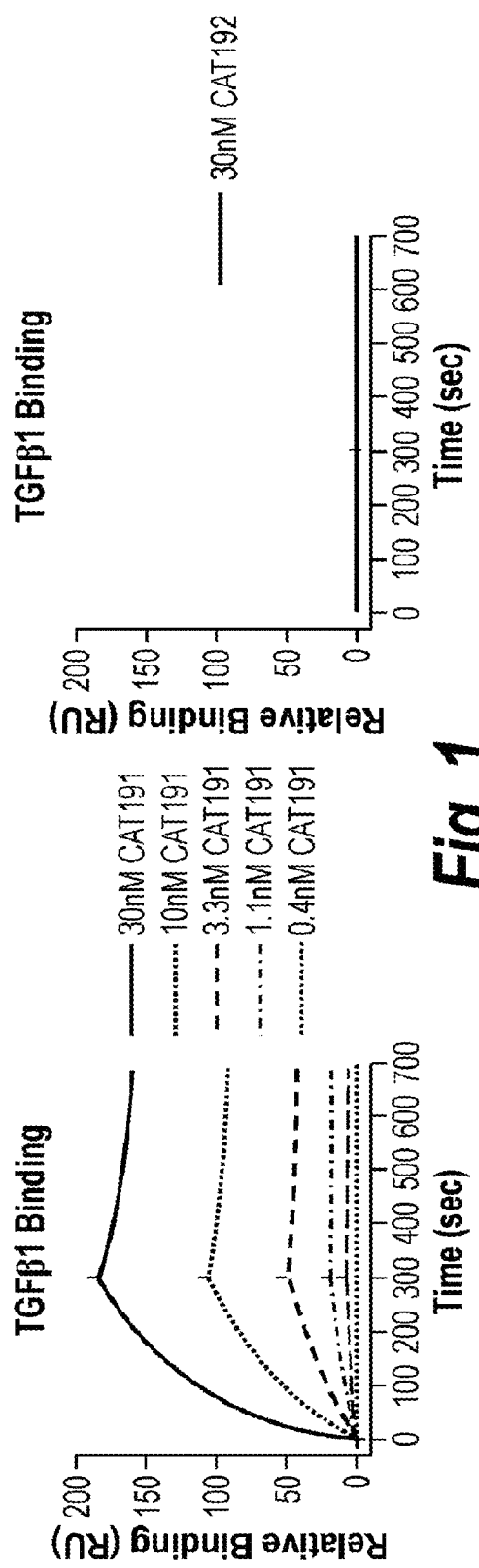
Figure 2:
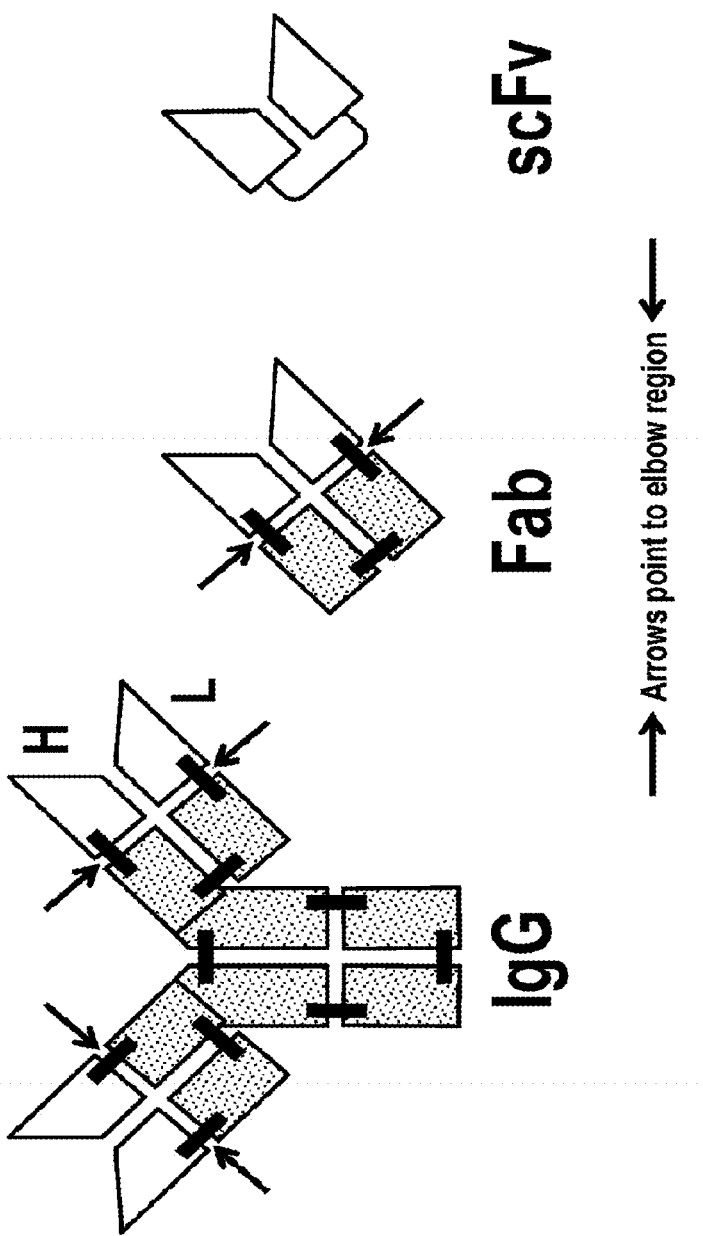
FIG. 2 depicts structural elements of a scFv, a Fab, an IgG molecule, and the elbow regions that were engineered to restore affinity.

The disclosed modified IgG antibodies bind and neutralize TGFβ1 selectively and with high affinity and avidity. The modified IgG antibodies may be composed of the same VH and VL domains as in metelimumab. The modified IgG antibodies advantageously show greater efficacy in neutralizing TGFβ1 than when the variable domains are used in other formats.

As used herein, a first element "and/or" a second element means a specific disclosure of the first or second element separately, or the first and second elements in combination. The singular forms "a," "an," and "the" include plural referents unless the context clearly dictates otherwise.

An "isolated" polynucleotide (or nucleic acid) or protein is removed and/or altered from its natural form using genetic engineering technologies. A "purified" nucleic acid or protein may be substantially pure, e.g., at least 90% pure, or in homogeneous form.

"Selective binding", or "binding selectively" to human TGFβ1, means that the binding protein (e.g., scFv-Fc dimer) is capable of binding human TGFβ1 with a higher affinity than binding to human TGFβ2 or human TGFβ3, e.g., with a dissociation constant with human TGFβ1 at least 50% lower than its dissociation constant with human TGFβ2 or human TGFβ3, as measured by surface plasmon resonance.

In one embodiment, the present modified IgG antibodies' variable domains comprise complementarity determining regions (CDRs) from the CDRs disclosed in U.S. Pat. No. 6,492,497 (e.g., SEQ ID Nos. 11-19 of U.S. Pat. No. 6,492,497), incorporated herein by reference. The CDR regions are listed below:

```
HCDR1
                           SEQ ID No. 7
SYMGH

HCDR2
                           SEQ ID No. 8
VISYDGSIKYYADSVKG

HCDR3
                           SEQ ID No. 9
TGEYSGYDTSGVEL

SEQ ID No. 10
TGEYSGYDTDPQYS

SEQ ID No. 11
TGFYSGYDTPASPD

LCDR1
                           SEQ ID No. 12
RASQGIGDDLG

LCDR2
                           SEQ ID No. 13
GTSTLQS

LCDR3
                           SEQ ID No. 14
LQDSNYPLT
```

Surprisingly, a consensus HCDR3 binding motif is revealed, having the sequence:

```
HCDR3
                           SEQ ID No. 15
TGX1YSGYDTX2X3X4X5X6
```

Wherein: $X_1$ may be any amino acid (preferably E, or F), or absent, $X_2$ may be any amino acid (preferably S, D, or P), or absent, $X_3$ may be any amino acid (preferably G, P, or A), or absent, $X_4$ may be any amino acid (preferably V, Q, or S), or absent, $X_5$ may be any amino acid (preferably E, Y, or P), or absent, $X_6$ may be any amino acid (preferably L, S, or D), or absent.

In one embodiment, the VH domain of the disclosed modified antibodies comprises a HCDR1 having the sequence of SEQ ID No. 7, a HCDR2 having the sequence of SEQ ID No. 8, and a HCDR3 having a sequence selected from the group consisting of SEQ ID No. 9, SEQ ID No. 10, SEQ ID No. 11, and SEQ ID No. 15. The CDR sequences may be separated by anywhere from one to four framework regions, in order from the N-terminal: FW1-CDR1-FW2-CDR2-FW3-CDR3-FW4. The framework regions of the VH domain may be selected from a variable heavy germline sequence. In one embodiment, the FW region sequences may be selected from the same human variable heavy germline sequence. The framework regions of the VL domain may be selected from a variable lambda or kappa germline sequence, e.g., from the same human variable lambda or kappa germline sequence. At present, about 40 variable heavy germline sequences are known in the art, as are about 40 variable kappa germline sequences and about 30 variable lambda germline sequences, e.g., $V_H3$, Vκ1, $V_H$ 1-69, and $V_H$ 1-e.

In another embodiment, composite VH or VL domains may be generated by using the CDR sequences disclosed herein. For example, crystal structures of the VH or VL domains may be used as a guidance to generate composite domain using CDR sequences from one antibody and using the germline FW regions from another antibody. More details can be found in U.S. Patent Application Publication No. 20020099179; and Homes and Foote, J Immunol. 1997 Mar. 1; 158(5):2192-201, both of which are hereby incorporated into this disclosure by reference.

The present modified IgG antibodies may be composed of the same VH and VL domains as in metelimumab, having the sequences set forth in SEQ ID No. 1 and SEQ ID No. 3, respectively. The VH domain may be replaced by the VH domain having the sequences set forth in SEQ ID No. 2; the VL domain may be replaced by the VL domain having the sequences set forth in SEQ ID No. 4. These VH and VL domains are disclosed in U.S. Pat. No. 6,492,497 (e.g., SEQ ID Nos. 4, 6, 8, and 10 of U.S. Pat. No. 6,492,497), incorporated herein by reference.

A "variable domain" (VD) refers to a hypervariable binding domain of an immunoglobulin, or a ligand binding domain of a receptor, involved in antigen/ligand binding as is known by persons skilled in the art. Variable domains are routinely referred to by their location or origin within an immunoglobulin; e.g., variable domains of the light chain of an immunoglobulin (VL), variable domains of the heavy chain of an immunoglobulin (VH), variable domains of the heavy chain of a camelid immunoglobulin (VHH).

A "variant" variable domain comprises amino acid additions, substitutions, and/or deletions, compared to the reference sequence. A "variant" of the VH or VL domains may have up to four such amino acid modifications. For example, one of the two domains may comprise an amino acid substitution, while the other domain is unmodified, or both of the domains may comprise amino acid substitutions. Modifications that add or delete amino acid residues may be made at the N-terminus or C-terminus of the VH or VL domain. For example, the N-terminal residue of the VH domain may be deleted.

For purpose of this disclosure, the terms "between," "from," "to," and "at least" are inclusive. For example, an integer "from 0 to 5" means any integer equal to or greater than 0 but equal to or smaller than 5.

In one embodiment, up to five amino acid substitutions may be made to de-immunize the modified IgG antibodies. De-immunization may be performed according to the method of Harding et al. (2010) mAbs 2: 256-265, for example.

Framework residues of the VH and/or VL domains, for example, may be substituted to increase the stability of the modified IgG antibodies and/or decrease their tendency to aggregate. Poor stability can affect the ability of the expressed modified IgG antibodies to fold properly when recombinantly expressed, resulting in a fraction of the expressed antibodies being non-functional. Low stability antibodies also may be prone to forming potentially immunogenic aggregates or may have impaired avidity or shelf-life. Framework amino acid substitutions that are expected to increase the stability and/or decrease the tendency to aggregate of a VH and/or VL domain, e.g., in a modified IgG antibody, are disclosed in WO 2007/109254, for example. Substitutions in corresponding residues in the present VH and VL domains are expected similarly to increase stability and/or decrease the tendency of modified IgG antibodies to aggregate.

Substitutions that can be tolerated are expected to include those that would replace an amino acid of SEQ ID No. 1, SEQ ID No. 2, SEQ ID No. 3, or SEQ ID No. 4 with a corresponding amino acid that occurs in another human VH or VL domain germline sequence. A substitution of a framework amino acid with an amino acid occurring in any of these germline sequences may be tolerated. For example, a residue of a VH domain of SEQ ID No. 1 may be substituted with an amino acid appearing in a corresponding position in any VH germline sequence, e.g., the germline sequence from DP-10 ($V_H$ 1-69) or DP-88 ($V_H$ 1-e). Corresponding positions in this case are determined by a sequence alignment between the various germline sequences, using alignment techniques well known in the art, e.g., ClustalW.

Additional substitutions that are expected to be tolerated are those made to an amino acid with most of its side chain exposed to the solvent, as determined by analysis of the three co-crystal structures. The solvent-accessible surface area of a residue may be estimated using techniques well known in the art. Further, it is expected that substitutions to amino acids buried within the variable domains will be better tolerated if the side chain of the amino acid does not create steric hindrance with adjoining residues. For this reason, buried amino acids generally are substituted with amino acids with side chains of similar or smaller size. For example, a substitution of a buried Ile residue with a Leu, Val, Ala, or Gly is expected to be tolerated. Possible steric hindrance created by a substitution can be predicted by analysis of the three co-crystal structures. Further substitutions that are expected to be tolerated are those maintaining existing electrostatic interactions within the variable domains, e.g., dipole-dipole interactions, induced dipole interactions, hydrogen bonds, or ionic bonds.

Additional amino acid substitutions of variable domains include those expected to confer new useful properties to the antibodies or antigen-binding fragments thereof. For example, putative N-glycosylation sites in the VH and/or VL domains can be removed to prevent or reduce the formation of N-glycoforms. The amino-terminal residue can be substituted with a Gln residue to cause pyroglutamylation, which can decrease the number of charge variants. Amino acid substitutions can be used to lower the isoelectric point, which can decrease the rate of elimination of IgG polypeptide antibodies, for example.

Surface residues of variable domains can be substituted with Cys or Lys residues, for example, which then can be covalently modified and coupled to molecules conferring useful characteristics to the antibodies or antigen-binding fragments thereof, e.g., a detectable label, toxin, targeting moiety, or protein. For example, Cys residue can be coupled to a cytotoxic drug to form a drug conjugate. Cys residues also can be coupled to molecules that increase the serum half-life, e.g., polyethylene glycol (PEG) or serum albumin. Such amino acid modifications are reviewed in Beck et al. (2010) Nature 10: 345-52, for example.

Detectable labels include radiolabels such as $^{131}$I or $^{99}$Tc, which may be attached to antibodies or antigen-binding fragments thereof using methods known in the art. Labels also include enzyme labels such as horseradish peroxidase. Labels further include chemical moieties such as biotin which may be detected via binding to a specific cognate detectable moiety, e.g., labeled avidin. Other moieties can be attached that facilitate purification. For example, antibodies or antigen-binding fragments thereof can be His-tagged using well-known methods of recombinant modification and expression.

The VL domains of the modified IgG antibodies are linked to the CL domains by a linker, termed Linker1 herein. The VH domains of the modified IgG antibodies are optionally linked to the CH1 domains by a second linker, termed Linker2 herein. Linkers suitable for making modified IgG antibodies are well known in the art. See, e.g., Bird et al. (1988) Science, 242: 423-426; Huston et al. (1988) Proc. Nat'l Acad. Sci. USA 85: 5879-5883. This can be accomplished by fusing the encoding nucleic acids in-frame and expressing the fusion protein in a suitable host cell, for example.

Linker1 may contain a peptide connecting the VL and CL in an IgG molecule, or a modified version with increased flexibility. For example, it may have the sequence of Leucine-Glutamic acid-Isoleucine-Lysine-$X_p$-$Y_q$-$Z_r$-Arginine-Threonine-Valine-Alanine, wherein X, Y and Z is independently an amino acid selected from the group consisting of Serine, Glycine, Alanine, Valine, Leucine, Isoleucine, and Threonine, and each of p, q and r is independently an integer from 0 to 5. Each of X, Y and Z is preferably Serine and Glycine, and each of p, q and r is 1. In another aspect, p is 0 and each of q and r is 1. In another aspect, p is 1 and each of q and r is 0.

Linker2 may contain a peptide having the sequence of Threonine-Valine-Serine-$A_d$-$B_e$-$C_f$-Serine-Alanine-Serine-Threonine, A, B and C being independently an amino acid selected from the group consisting of Serine, Glycine, Alanine, Valine, Leucine, Isoleucine, and Threonine, and each of d, e and f being independently an integer from 0 to 5.

In another embodiment, a hinge is optionally inserted between the CH1 domain and Fc region of the modified IgG antibodies. In one aspect, the hinge region is a flexible domain that optionally joins the CH1 portion to the Fc region. The flexibility of the hinge region in IgG molecules may allow the Fab arms to adopt a wide range of angles, permitting binding to epitopes spaced variable distances apart. In another aspect, a suitable hinge region includes, for example, the human IgG1 hinge region having the amino acid sequence PKSCDKTHTCPPCPAPELLGGP (SEQ ID No. 5). This sequence corresponds to a portion of the human IgG1 upper hinge, the middle hinge, and an N-terminal portion of the $CH_2$ domain, as disclosed in FIG. 4B of U.S. Pat. No. 8,048,421, for example.

In another embodiment, suitable Fc regions of the modified IgG antibodies contain two or three constant regions. Fc regions may include those from human IgG1, as set forth in SEQ ID No. 6, or IgG4, as set forth in the $CH_2$ and $CH_3$ domains of SEQ ID No. 17. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP).

Modifications can be made to the hinge and Fc region to improve various properties of the modified IgG antibodies. In one embodiment, one, two, three, four, five or up to ten amino acids of a naturally occurring human Fc region can be modified, in addition to modifications of the hinge region. For example, the Fc region can be modified to increase the serum half-life of the modified IgG antibodies. The half-life of an IgG depends on its pH-dependent binding to the receptor FcRn. FcRn, which is expressed on the surface of endothelial cells, binds the IgG in a pH-dependent manner and protects it from degradation. Mutations located at the interface between the $CH_2$ and $CH_3$ domains, for example, have been shown to increase the binding affinity to FcRn and the half-life of IgG1 in vivo. Such modifications are reviewed in Strohl W R., 2009. Optimization of Fc-mediated effector functions of monoclonal antibodies. Curr Opin Biotechnol. 20(6):685-91; and Vaccaro C. et al., 2005.

Engineering the Fc region of immunoglobulin G to modulate in vivo antibody levels. Nat Biotechnol. 23(10):1283-8, for example.

Other modifications to the hinge and/or Fc region can increase or reduce effector functions. The four human IgG isotypes bind the activating Fcγ receptors (FcγRI, FcγRIIa, FcγRIIIa), the inhibitory FcγRIIb receptor, and the first component of complement (C1q) with different affinities, resulting in different effector functions. Binding of IgG to the FcγRs or C1q, for example, depends on residues located in the IgG hinge region and $CH_2$ domain. Single or multiple amino acid substitutions of these residues can affect effector function by modulating the IgG interaction with FcγRs or C1q. Other substitutions are known to affect effector function. These modifications are reviewed in Strohl (2009) "Optimization of Fc-mediated effector functions of monoclonal antibodies," Curr. Opin. Biotechnol. 20:685-91, for example.

Representative modifications of the hinge and/or Fc region are summarized in Table 1.

82: 1090-99 disclose engineering the IgG2 hinge region to limit disulfide bond scrambling and the formation of structural isomers in therapeutic applications. Amino acid modifications to a CH3 domain also can be used to delete carboxy-terminal Lys residues to decrease the number of charge variants. Amino acid modifications also can be used to improve the pharmacological function of recombinant antibodies or antigen-binding fragments thereof. For example, amino acid modifications can be used to increase complement activation, enhance antibody-dependent cellular cytotoxicity (ADCC) by increasing FcγRIIIA binding or decreasing FcγRIIIB binding, and/or increase serum half-life by increasing FcRn binding. Such amino acid modifications are reviewed in Beck et al. (2010) Nature 10: 345-52, for example.

Nucleic Acids and Methods of Making Modified IgG Antibodies

A further aspect of the present invention provides nucleic acids encoding modified IgG antibodies. The isolated

TABLE 1

Representative Hinge and Fc Region Modifications

| Isotype | Species | Substitutions | FcR/C1q Binding | Effector Function | Refs |
|---|---|---|---|---|---|
| IgG1 | Human | T250Q/M428L | Increased binding to FcRn | Increased half-life | 1 |
| IgG1 | Human | 1M252Y/S254T/T256E + H433K/N434F | Increased binding to FcRn | Increased half-life | 2 |
| IgG1 | Human | E233P/L234V/L235A/G236 + A327G/A330S/P331S | Reduced binding to FcγRI | Reduced ADCC and CDC | 3, 4 |
| IgG1 | Human | E333A | Increased binding to FcγRIIIa | Increased ADCC and CDC | 5, 6 |
| IgG1 | Human | S239D/A330L/I332E | Increased binding to FcγRIIIa | Increased ADCC | 7, 8 |
| IgG1 | Human | P257I/Q311 | Increased binding to FcRn | Unchanged half-life | 9 |
| IgG1 | Human | K326W/E333S | Increased binding to C1q | Increased CDC | 10 |
| IgG1 | Human | S239D/I332E/G236A | Increased FcγRIIa/FcγRIIb ratio | Increased macrophage phagocytosis | 11 |
| IgG1 | Human | K322A | Reduced binding to C1q | Reduced CDC | 5 |
| IgG4 | Human | S228P | — | Reduced Fab-arm exchange | 12 |
| IgG2a | Mouse | L235E + E318A/K320A/K322A | Reduced binding to FcγRI and C1q | Reduced ADCC and CDC | 10 |

1. Hinton et al. (2004) J. Biol. Chem. 279(8): 6213-16.
2. Vaccaro et al. (2005) Nature Biotechnol. 23(10): 1283-88.
3. Armour et al. (1999) Eur. J. Immunol. 29(8): 2613-24.
4. Shields et al. (2001) J. Biol. Chem. 276(9): 6591-604.
5. Idusogie et al. (2000) J. Immunol. 164(8): 4178-84.
6. Idusogie et al. (2001) J. Immunol. 166(4): 2571-75.
7. Lazar et al. (2006) Proc. Nat'l Acad. Sci. USA 103(11): 4005-10.
8. Ryan et al. (2007) Mol. Cancer Ther. 6: 3009-18.
9. Datta-Mannan et al. (2007) Drug Metab. Dispos. 35: 86-94.
10. Steurer et al. (1995) J. Immunol. 155(3): 1165-74.
11. Richards et al. (2008) Mol. Cancer Ther. 7(8): 2517-27.
12. Labrijn et al. (2009) Nature Biotechnol. 27(8): 767-71.

Further, recombinant amino acid modifications can be used to decrease structural homogeneity of the expressed polypeptides. A representative example is Peters et al. (2012) J. Biol. Chem. 287(29): 24525-33, which discloses Cys to Ser substitutions in the IgG4 hinge region that reduce the disulfide bond heterogeneity and increase Fab domain thermal stability. Similarly, Zhang et al. (2010) Anal. Chem. nucleic acid may be a synthetic DNA, a non-naturally occurring mRNA, or a cDNA, for example. Examples include the nucleic acids encoding the VH and VL domains set forth in SEQ ID NOS: 3, 5, 7, and 9 of U.S. Pat. No. 6,492,497. A recombinant host cell may comprise one or more constructs above. Methods of preparing modified IgG antibodies comprise expressing the encoding nucleic acid in a host cell under conditions to produce the modified IgG antibodies, and recovering the antibodies. The process of recovering the antibodies may comprise isolation and/or purification of the antibodies. The method of production may comprise formulating the antibodies into a composition including at least one additional component, such as a pharmaceutically acceptable excipient.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line $E.$ $coli$; mammalian cell lines CHO, HEK 293 and COS; the insect cell line Sf9; and the fungal cell $Saccharomyces$ $cerevisiae$.

Suitable vectors comprising a nucleic acid encoding modified IgG antibodies can be chosen or constructed, containing appropriate regulatory sequences, including promoter sequences, terminator sequences, polyadenylation sequences, enhancer sequences, marker genes and other sequences as appropriate. Vectors may be plasmids, phage, phagemids, adenoviral, AAV, lentiviral, for example. Techniques and protocols for manipulation of nucleic acid, for example in preparation of nucleic acid constructs, mutagenesis, sequencing, introduction of DNA into cells, and gene expression, are well known in the art.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adena-associated viruses), which serve equivalent functions.

Introducing such nucleic acids into a host cell can be accomplished using techniques well known in the art. For eukaryotic cells, suitable techniques may include calcium phosphate transfection, DEAE-Dextran, electroporation, liposome-mediated transfection, and transduction using retroviruses or other viruses, for example. For bacterial cells, suitable techniques may include calcium chloride transformation, electroporation, and transfection using bacteriophage. The introduction may be followed by causing or allowing expression from the nucleic acid, e.g. by culturing host cells under conditions for expression of the gene. In one embodiment, the nucleic acid of the invention is integrated into the genome, e.g., chromosome, of the host cell. Integration may be promoted by inclusion of sequences which promote recombination with the genome, in accordance with standard techniques.

Systems for cloning and expression of a polypeptide in a variety of different host cells are well known. Suitable host cells include bacteria, mammalian cells, plant cells, insect cells, fungi, yeast and transgenic plants and animals. Mammalian cell lines available in the art for expression of a heterologous polypeptide include Chinese hamster ovary (CHO) cells, HeLa cells, baby hamster kidney cells, mouse melanoma cells, rat myeloma cells, human embryonic kidney cells, e.g., HEK293 cells, human embryonic retina cells, and many others. The expression of antibodies and antibody fragments in prokaryotic cells, such as $E.$ $coli$, is well established in the art. For a review, see for example, Plückthun $Bio/Technology$ 9: 545-551 (1991). Expression in cultured eukaryotic cells is also available to those skilled in the art, as reviewed in Andersen et al. (2002) $Curr.$ $Opin.$ $Biotechnol.$ 13: 117-23, for example.

In another embodiment, the disclosed modified IgG antibodies may be glycosylated, either naturally or the choice of expression host, e.g., CHO, HEK293, or NSO (ECACC 85110503) cells, or they may be unglycosylated, for example if produced by expression in a prokaryotic cell. Glycosylation may also be intentionally altered, for example by inhibiting fucosylation, in order to increase ADCC activity of the resulting modified IgG antibodies.

Methods of Using Antibodies or Antigen-Binding Fragments Thereof

The modified IgG antibodies may be used in a method of treatment or diagnosis of the human or animal body, such as a method of treatment (which may include prophylactic treatment) of a disease or disorder in a human patient, which comprises administering an effective amount to treat the patient. Treatable conditions include any in which TGFβ1 plays a role, e.g., a fibrotic disease, cancer, an immune-mediated disease, and wound healing, e.g., diffuse systemic sclerosis, bone remodeling disease, kidney disease and/or a combination thereof.

Antibodies specific for human TGFβ1 have been shown to be effective in animal models for the treatment of TGFβ1 glomerulonephritis (Border et al. (1990) $Nature$ 346: 371-374), neural scarring (Logan et al. (1994) $Eur.$ $J.$ $Neurosci.$ 6: 355-363), dermal scarring (Shah et al. (1992) $Lancet$ 339: 213-214; Shah et al. (1994) $J.$ $Cell$ $Science$ 107: 1137-1157; Shah et al. (1995) $J.$ $Cell$ $Science$ 108: 985-1002), and pulmonary fibrosis (Gini et al. (1993) $Thorax$ 48: 959-966). Further, antibodies to TGFβ1, 2, and 3 have been shown to be effective in models of lung fibrosis, radiation induced fibrosis (U.S. Pat. No. 5,616,561), myelofibrosis, burns, Dupuytren's contracture, gastric ulcers, and rheumatoid arthritis (Wahl et al. (1993) $Exp.$ $Medicine$ 177: 225-230).

The modified IgG antibodies are useful to treat a disease and condition resulting directly or indirectly from TGFβ1 activity. The modified IgG antibodies may selectively inhibit the activity of a human TGFβ1 isoform in vitro or in vivo. Activities of TGFβ1 isoforms include, but are not limited to, TGFβ-mediated signaling, extracellular matrix (ECM) deposition, inhibiting epithelial and endothelial cell proliferation, promoting smooth muscle proliferation, inducing Type III collagen expression, inducing TGF-β, fibronectin, VEGF, and IL-11 expression, binding Latency Associated Peptide, tumor-induced immunosuppression, promotion of angiogenesis, activating myofibroblasts, promotion of metastasis, and inhibition of NK cell activity. For example, the modified IgG antibodies are useful to treat focal segmental glomerulosclerosis (FSGS), hepatic fibrosis (HF), acute myocardial infarction (AMI), idiopathic pulmonary fibrosis (IPF), scleroderma (SSc), and Marfan Syndrome.

The modified IgG antibodies are useful to treat diseases and conditions including, but not limited to, fibrotic diseases (such as glomerulonephritis, neural scarring, dermal scarring, pulmonary fibrosis, lung fibrosis, radiation induced fibrosis, hepatic fibrosis, myelofibrosis), burns, immune mediated diseases, inflammatory diseases (including rheumatoid arthritis), transplant rejection, cancer, Dupuytren's contracture, and gastric ulcers. The modified IgG antibodies are also useful for treating, preventing and reducing the risk of occurrence of renal insufficiencies including but not limited to: diabetic (type I and type II) nephropathy, radiation-induced nephropathy, obstructive nephropathy, diffuse systemic sclerosis, pulmonary fibrosis, allograft rejection, hereditary renal disease (e.g., polycystic kidney disease, medullary sponge kidney, horseshoe kidney), glomerulonephritis, nephrosclerosis, nephrocalcinosis, systemic lupus erythematosus, Sjogren's syndrome, Berger's disease, systemic or glomerular hypertension, tubulointerstitial nephropathy, renal tubular acidosis, renal tuberculosis, and renal infarction. In particular, the modified IgG antibodies are useful when combined with antagonists of the renin-angiotensin-aldosterone system including, but not limited to: renin inhibitors, angiotensin-converting enzyme (ACE) inhibitors, Ang II receptor antagonists (also known as "Ang II receptor blockers"), and aldosterone antagonists. By way of example, methods for using modified IgG antibodies in combination with such antagonists are set forth in WO 2004/098637.

The modified IgG antibodies also are useful to treat diseases and conditions associated with the deposition of ECM, including, systemic sclerosis, postoperative adhesions, keloid and hypertrophic scarring, proliferative vitreoretinopathy, glaucoma drainage surgery, corneal injury, cataract, Peyronie's disease, adult respiratory distress syndrome, cirrhosis of the liver, post myocardial infarction scarring, post angioplasty restenosis, scarring after subarachnoid hemorrhage, multiple sclerosis, fibrosis after laminectomy, fibrosis after tendon and other repairs, scarring due to tattoo removal, biliary cirrhosis (including sclerosing cholangitis), pericarditis, pleurisy, tracheostomy, penetrating central nervous system injury, eosinophilic myalgic syndrome, vascular restenosis, veno-occlusive disease, pancreatitis and psoriatic arthropathy.

The modified IgG antibodies further are useful to promote re-epithelialization in diseases and conditions such as venous ulcers, ischaemic ulcers (pressure sores), diabetic ulcers, graft sites, graft donor sites, abrasions and burns, diseases of the bronchial epithelium, such as asthma, ARDS, diseases of the intestinal epithelium, such as mucositis associated with cytotoxic treatment, esophageal ulcers (reflux disease), stomach ulcers, small intestinal and large intestinal lesions (inflammatory bowel disease).

The modified IgG antibodies also may be used to promote endothelial cell proliferation, for example, in stabilizing atherosclerotic plaques, promoting healing of vascular anastomoses, or to inhibit smooth muscle cell proliferation, such as in arterial disease, restenosis and asthma.

The modified IgG antibodies are useful to enhance the immune response to macrophage-mediated infections. They are also useful to reduce immunosuppression caused, for example, by tumors, AIDS, or granulomatous diseases. The modified IgG antibodies are useful to treat hyperproliferative diseases, such as cancers including, but not limited to, breast, prostate, ovarian, stomach, renal, pancreatic, colorectal, skin, lung, cervical and bladder cancers, glioma, mesothelioma, as well as various leukemias and sarcomas, such as Kaposi's sarcoma, and are useful to treat or prevent recurrences or metastases of such tumors. Modified IgG antibodies also are useful to inhibit cyclosporin-mediated metastases.

In the context of cancer therapy, "treatment" includes any medical intervention resulting in the slowing of tumor growth or reduction in tumor metastases, as well as partial remission of the cancer in order to prolong life expectancy of a patient.

Methods of treatment comprise administering a modified IgG antibody or pharmaceutical compositions comprising the modified IgG antibody. The modified IgG antibodies may be used in the manufacture of a medicament for administration. For example, a method of making a medicament or pharmaceutical composition comprises formulating a modified IgG antibody with a pharmaceutically acceptable excipient. A composition may be administered alone or in combination with other treatments, either simultaneously or sequentially dependent upon the condition to be treated.

Administration is preferably in a "therapeutically effective amount" sufficient to show benefit to a patient. Such benefit may be at least amelioration of at least one symptom of a particular disease or condition. The actual amount administered, and rate and time-course of administration, will depend on the nature and severity of the disease or condition being treated. Prescription of treatment, e.g., decisions on dosage etc., may be determined based on preclinical and clinical studies the design of which is well within the level of skill in the art.

The precise dose will depend upon a number of factors, including whether the modified IgG antibody is for diagnosis or for treatment, the size and location of the area to be treated, and the nature of any detectable label or other molecule attached to the modified IgG antibody. A typical dose of a modified IgG antibody, for example, can be in the range 100 µg to 1 gram for systemic applications, and 1 µg to 1 mg for topical applications. The dose for a single treatment of an adult patient may be adjusted proportionally for children and infants. Treatments may be repeated at daily, twice-weekly, weekly, monthly or other intervals, at the discretion of the physician. Treatment may be periodic, and the period between administrations is about two weeks or more, preferably about three weeks or more, more preferably about four weeks or more, or about once a month.

In one embodiment, dose levels of about 0.1, 0.3, 1, 3, 10, 15 mg, or 20 mg of the disclosed antibodies per kg body weight of the patient may be useful and safe in humans. For example, 0.5-5 mg/kg in rat and mouse has been an effective dose in an acute setting. Therefore, for long-term dosing, 0.3-10 mg/kg may be administered to humans, based on an expected half-life of 21 days. Doses may be sufficient for efficacy, while low enough to facilitate optimal administration. For example, a dose of less than 50 mg facilitates subcutaneous administration. Intravenous administration may be used as the route of delivery for severe diseases, where high doses and the long dosing intervals may be required. Subcutaneous injection can increase the potential immune response to a product. Local administration for localized disease can reduce the amount of administered product and increase the concentration at the site of action, which can improve safety.

Modified IgG antibodies may be administered by injection, for example, subcutaneously, intravenously, intracavity (e.g., after tumor resection), intralesionally, intraperitoneally, or intramuscularly. Modified IgG antibodies also may be delivered by inhalation or topically (e.g., intraocular, intranasal, rectal, into wounds, on skin), or orally.

A modified IgG antibody will usually be administered in the form of a pharmaceutical composition, which may comprise at least one component in addition to the modified IgG antibody. Thus pharmaceutical compositions may comprise a pharmaceutically acceptable excipient, carrier, buffer, stabilizer or other materials well known to those skilled in the art. Such materials should be non-toxic and should not interfere with the efficacy of the active ingredient. Such materials could include, for example, any and all solvents, dispersion media, coatings, antibacterial and antifungal agents, isotonic, and absorption delaying agents. Some examples of pharmaceutically acceptable carriers are water, saline, phosphate buffered saline, dextrose, glycerol, ethanol, and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives, or buffers, which increase the shelf life or effectiveness.

The precise nature of the carrier or other material will depend on the route of administration. For intravenous injection, or injection at the site of affliction, the active ingredient will be in the form of a parenterally acceptable aqueous solution which is pyrogen-free and has suitable pK, isotonicity, and stability. Those of relevant skill in the art are well able to prepare suitable solutions using, for example, isotonic vehicles such as sodium chloride injection, Ringer's injection, and lactated Ringer's injection. Preservatives, stabilizers, buffers, antioxidants, and/or other additives may be included.

A modified IgG antibody may be formulated in liquid, semi-solid, or solid forms, such as liquid solutions (e.g., injectable and infusible solutions), dispersions or suspensions, powders, liposomes, and suppositories. The preferred form depends on the intended mode of administration, the therapeutic application, the physicochemical properties of the molecule, and the route of delivery. Formulations may include excipients, or a combination of excipients, for example: sugars, amino acids and surfactants. Liquid formulations may include a wide range of modified IgG antibody concentrations and pH. Solid formulations may be produced by lyophilization, spray drying, or drying by supercritical fluid technology, for example.

Therapeutic compositions can be formulated as a solution, microemulsion, dispersion, liposome, or other ordered structure suitable to high drug concentration. Sterile injectable solutions can be prepared by incorporating the modified IgG antibody in an appropriate solvent with one or a combination of ingredients enumerated above, followed by filtered sterilization. Generally, dispersions are prepared by incorporating the active compound into a sterile vehicle that contains a basic dispersion medium and other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by using a coating such as lecithin, by maintaining the particle size of a dispersion, or by using surfactants. Prolonged absorption of injectable compositions can be brought about by including in the composition an agent that delays absorption, for example, monostearate salts and gelatin.

In certain embodiments, the active compound may be prepared with a carrier that will protect the modified IgG antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

A method of using a modified IgG antibody may comprise causing or allowing binding to TGFβ. Such binding may take place in vivo, e.g., following administration of a modified IgG antibody to a patient, or it may take place in vitro, e.g., in ELISA, Western blotting, immunocytochemistry, immunoprecipitation, affinity chromatography, or cell based assays, or in ex vivo based therapeutic methods, e.g., methods in which cells or bodily fluids are contacted ex vivo with a modified IgG antibody and then administered to a patient.

A kit comprising a modified IgG antibody is provided. The modified IgG antibody may be labeled to allow its reactivity in a sample to be determined. Kits may be employed in diagnostic analysis, for example. A kit may contain instructions for use of the components. Ancillary materials to assist in or to enable performing such a method may be included within the kit.

The reactivity of a modified IgG antibody in a sample may be determined by any appropriate means, e.g., radioimmunoassay (RIA). Radioactively labeled antigen may be mixed with unlabeled antigen (the test sample) and allowed to bind to the modified IgG antibody. Bound antigen is physically separated from unbound antigen and the amount of radioactive antigen bound to the modified IgG antibody is determined. A competitive binding assay also may be used with non-radioactive antigen, using an antigen or an analogue linked to a reporter molecule. The reporter molecule may be a fluorochrome, phosphor, or dye. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are colored, magnetic or paramagnetic, and biologically or chemically active agents that can directly or indirectly cause detectable signals to be visually observed, electronically detected or otherwise recorded. These molecules may be enzymes that catalyze reactions that develop or change colors or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. The signals generated by antibody-reporter conjugates may be used to derive quantifiable absolute or relative data of the relevant antibody binding in samples.

The present invention also provides the use of a modified IgG antibody for measuring antigen levels in a competition assay. The modified IgG antibody can be linked to a reporter molecule so that a physical or optical change occurs on binding, for example. The reporter molecule may directly or indirectly generate detectable, and preferably measurable, signals. The reporter molecules may be linked directly or indirectly, covalently, e.g., via a peptide bond or non-covalently. The modified IgG antibody and a protein reporter may be linked by a peptide bond and recombinantly expressed as a fusion protein.

Further aspects and embodiments of the present invention will be apparent to those skilled in the art in the light of the present disclosure, including the following experimental exemplification.

EXAMPLES

Example 1: Modified IgG4 Antibody with Additional Amino Acids in the Light Chain Elbow Region CAT192 is a TGFβ1-specific antibody, but most of its binding affinity was lost when it was converted from a scFv into a full-length IgG4 (FIG. 1). Antibody subtype and Fc formats alone do not explain this phenomenon because both IgG1 and IgG4 Fab displayed very low affinity to TGFβ1. The tight binding of scFv to TGFβ1 may be due to the high flexibility resulting from the long (GGGGS)$_3$ (SEQ ID NO:64) linker connecting the heavy and light chain Fv domains. This high flexibility may have been lost during conversion of the scFv to Fab or IgG versions. The low affinity of CAT192 was characterized by a very slow on-rate but also a very slow off-rate. The slow on-rate and off-rate suggested that the binding between CAT192 and TGFβ1 may require a potential conformational change which was limited by unfavorable amino acids in CAT192 (IgG4). Described here are experiments designed to increase flexibility/affinity of the Fab or IgG versions of the scFv by adding additional amino acids in the light chain elbow region, which links the antibody Fv domain to the CH1 domain. More specifically, mutants were designed to add one glycine (G), two glycines (GG), two glycines and one serine (GGS), three glycines and one serine (GGGS; SEQ ID NO: 62), and four glycines and one serine (GGGGS; SEQ ID NO: 63) sequences into the wild-type light chain elbow region as shown below in Table 2, with the added amino acids underlined.

TABLE 2

Modified-IgG4 Light Chain Elbow Region Insertion Mutants

| Name | Position | Amino acid sequence |
|---|---|---|
| WT | Light chain elbow region | LEIKRTVA (SEQ ID No. 21) |
| LC + G | Light chain elbow region | LEIK<u>G</u>RTVA (SEQ ID No. 22) |
| LC + GG | Light chain elbow region | LEIK<u>GG</u>RTVA (SEQ ID No. 23) |
| LC + GGS | Light chain elbow region | LEIK<u>GGS</u>RTVA (SEQ ID No. 24) |
| LC + GGGS | Light chain elbow region | LEIK<u>GGGS</u>RTVA (SEQ ID No. 25) |
| LC + GGGGS | Light chain elbow region | LEIK<u>GGGGS</u>RTVA (SEQ ID No. 26) |
| A25S | Light chain Fv | Ala25→Ser25 |

The light chain amino acid #25 is an Ala in scFv, but was changed to Ser when converted to IgG4. Therefore, an additional A25S mutant was included as a control to test whether changing the Ala to Ser affects the affinity of the scFv to TGFβ1. The wild-type CAT192 and the mutant DNA and amino acid sequences are listed below.

SEQ ID No. 38: Amino acid sequence of CAT192 IgG1 Wild-Type LC with
the elbow region underlined:
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKR

TVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGE

C

SEQ ID No. 27: Coding sequence of CAT192 (IgG1) Light Chain
atgggctggtcctgcatcatcctgtttctggtggccacagccaccggcgtgcacagcGAGATCGTGCTGACA

CAGAGCCCCAGCAGCCTGTCTGCCAGCGTGGGCGACAGAGTGACCATCAC

CTGTAGAGCCAGCCAGGGCATCGGCGACGACCTGGGATGGTATCAGCAGA

AGCCTGGCAAGGCCCCCATCCTGCTGATCTACGGCACCAGCACACTGCAG

-continued
```
AGCGGCGTGCCCTCCAGATTTTCTGGCAGCGGCTCCGGCACCGACTTCACC

CTGACCATCAACAGCCTGCAGCCCGAGGACTTCGCCACCTACTACTGTCTG

CAAGACAGCAACTACCCCCTGACCTTCGGCGGAGGCACCCGGCTGGAAAT

CAAGCGTACGGTGGCCGCTCCTTCCGTGTTCATCTTCCCTCCCTCCGACGA

GCAGCTGAAGTCCGGCACCGCCTCCGTGGTGTGTCTGCTGAACAACTTCTA

CCCTCGGGAGGCCAAGGTGCAGTGGAAGGTGGACAACGCCCTGCAGTCCG

GCAACTCCCAGGAGTCCGTCACCGAGCAGGACTCCAAGGACAGCACCTAC

TCCCTGTCCTCCACCCTGACCCTGTCCAAGGCCGACTACGAGAAGCACAA

GGTGTACGCCTGTGAGGTGACCCACCAGGGCCTGTCCAGCCCTGTGACCA

AGTCCTTCAACCGGGGCGAGTGCTGA
```

CAT192LC + G (LEIKGRTVA)

(SEQ ID No. 28)

Forward 5'-ggctggaaatcaagggccgtacggtggccgc-3'

(SEQ ID No. 29)

Complement 5'-gcggccaccgtacggcccttgatttccagcc-3'

CAT192LC + GG. (LEIKGGRTVA)

(SEQ ID No. 30)
Forward 5'-ggctggaaatcaagggcggccgtacggtggccgc-3'

(SEQ ID No. 31)
Complement 5'-gcggccaccgtacggccgcccttgatttccagcc-3'

CAT192LC + GGS. (LEIKGGSRTVA)

(SEQ ID No. 32)
Forward 5'-ggctggaaatcaagggcggcagccgtacggtggccgc-3'

(SEQ ID No. 33)
Complement 5'-gcggccaccgtacggctgccgcccttgatttccagcc-3'

CAT192LC + GGGS. (LEIKGGGSRTVA)

(SEQ ID No. 34)
Forward 5'-ggctggaaatcaagggcggcggcagccgtacggtggccgc-3'

(SEQ ID No. 35)
Complement 5'-gcggccaccgtacggctgccgccgcccttgatttccagcc-3'

CAT192LC + GGGGS. (LEIKGGGGSRTVA)

(SEQ ID No. 36)
Forward 5'-ggctggaaatcaagggcggcggcggcagccgtacggtggccgc-3'

(SEQ ID No. 37)
Complement 5'-gcggccaccgtacggctgccgccgccgcccttgatttccagcc-3'

The five CAT192 LC mutants, along with the A25S mutant and WT LC were co-expressed with His-tagged CAT192 HC Fab using the Expi293F transfection system (Life Technologies) in a 24-well plate format (4×1 mL). Conditioned media (CM) was harvested 4 days post-transfection and the Octet QK384 instrument was used to calculate expression level and TGFβ1 binding in a single assay. Purified CAT192 Fab-His was used as a standard curve (diluted 2-fold from 100 to 3.125 μg/mL). The CAT192 Fab CM was diluted 1:10 in diluent and GC1008 Fab CM was included as positive control. Binding to anti-Fab-CH1 biosensors was measured for 2 min at 1000 rpm and 30° C. plate temperature for quantitation and capture. The sensors were then moved into wells containing 200 nM of TGFβ1 for binding assessment.

The TGFβ1 binding result showed that each additional amino acid insertion increased the binding affinity of the CAT192 Fab as compared to the WT counterpart. Addition of at least two glycines increased the binding affinity to a level comparable to that of the GC1008 Fab antibody. The A25S mutant showed weak TGFβ1 binding affinity, similar to the affinity of the WT and the purified recombinant CAT192 Fab. This result was qualitative because the amount of Fab captured to the sensors was not normalized for concentration or buffer subtracted.

The CAT192 LC Fab variants were then purified using PureSpeed IMAC tips from Rainin in order to accurately assess the affinity to TGFβ1 and confirm isoform-specificity using surface plasmon resonance. The conditioned media for each sample was split into four wells (~800 μL each) and ~200 μL equilibration buffer was added to each in order to use two 1 mL purification tips (20 μL resin) for each sample. The samples were buffer exchanged using Amicon Ultra filters into Gibco PBS pH 7.2 after the elution step to remove the imidazole. The concentrations were measured by A280 and 3.5 μg was loaded onto a non-reducing 4-20% Tris-Glycine SDS-PAGE gel and Coomassie stained to check the purity. The overall yield ranged from 12-42% of the starting material in CM.

Figure 6:
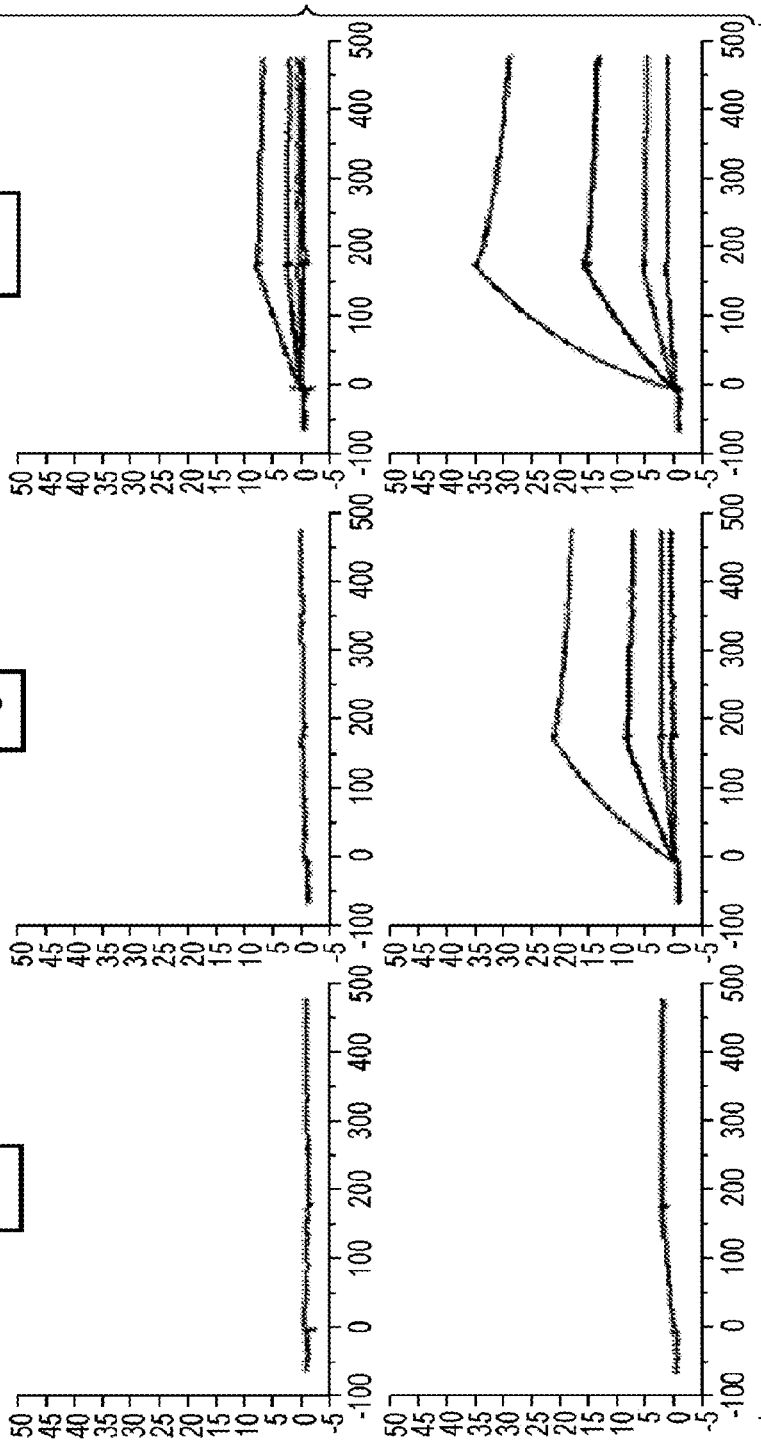
FIG. 6 depicts a Biacore TGFβ1 binding assay which shows high affinity binding is regained when additional amino acids are inserted into the elbow region of both the heavy and light chain of CAT192 Fab.
Figure 6:
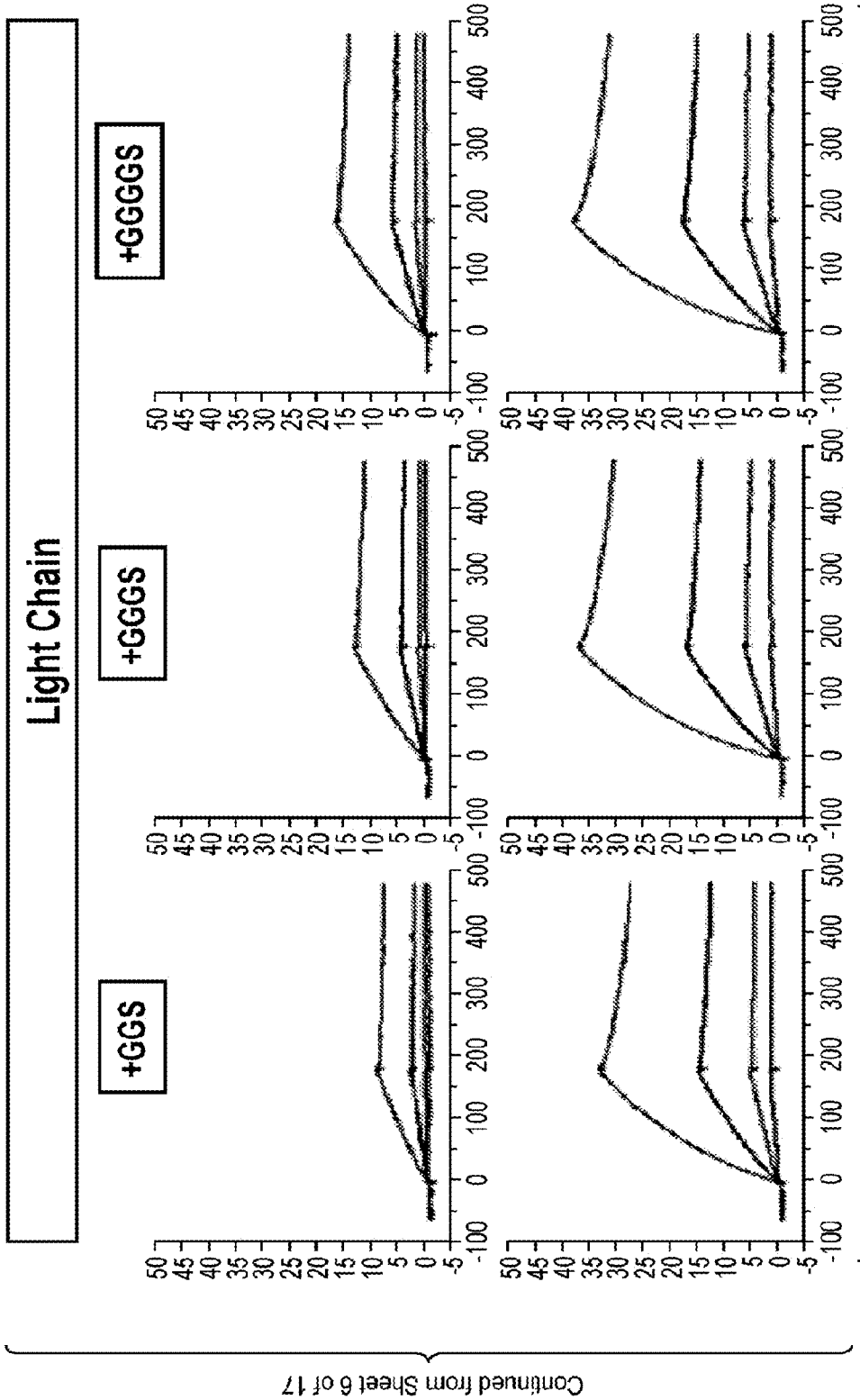
Figure 6:
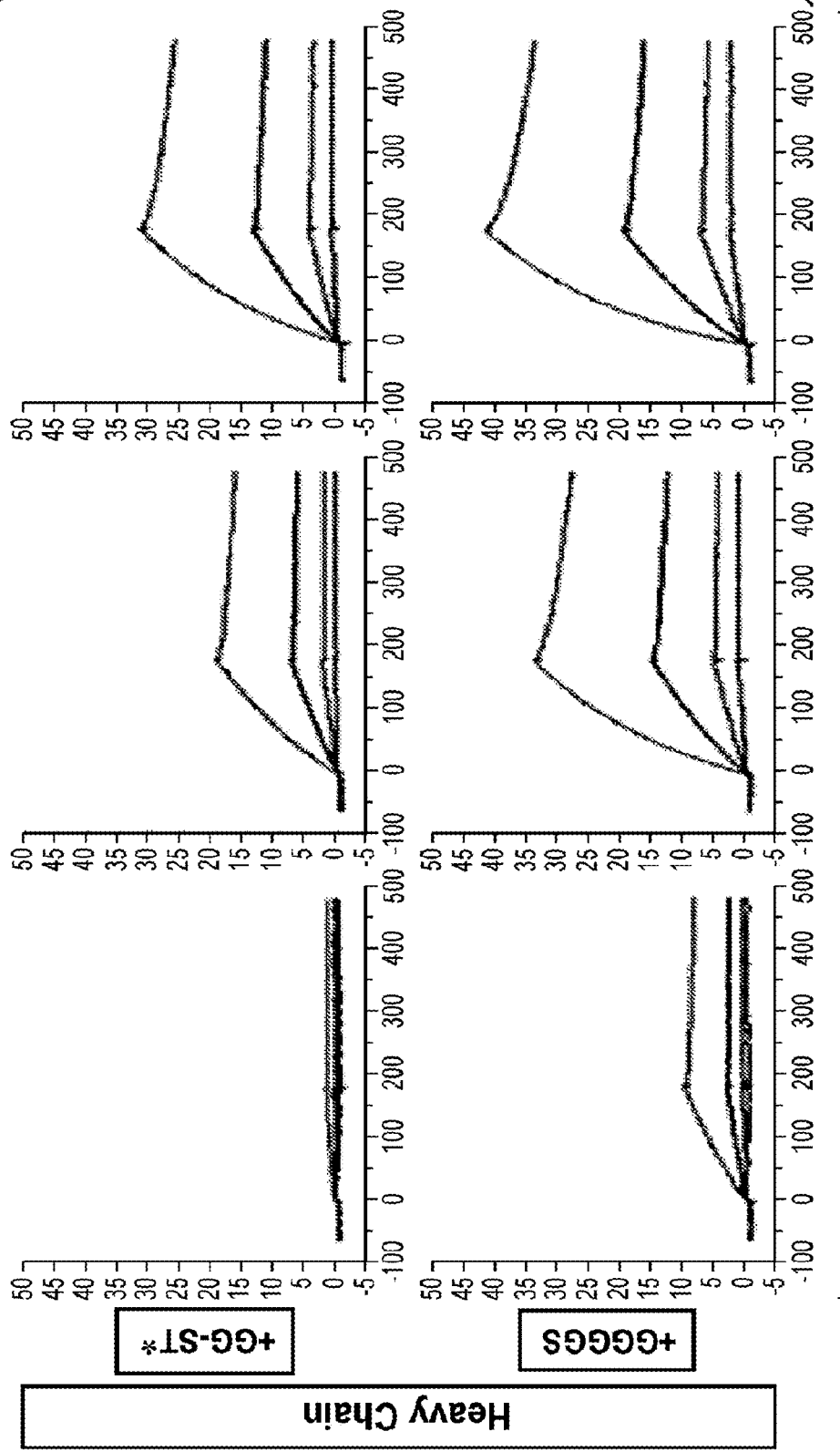
Figure 6:
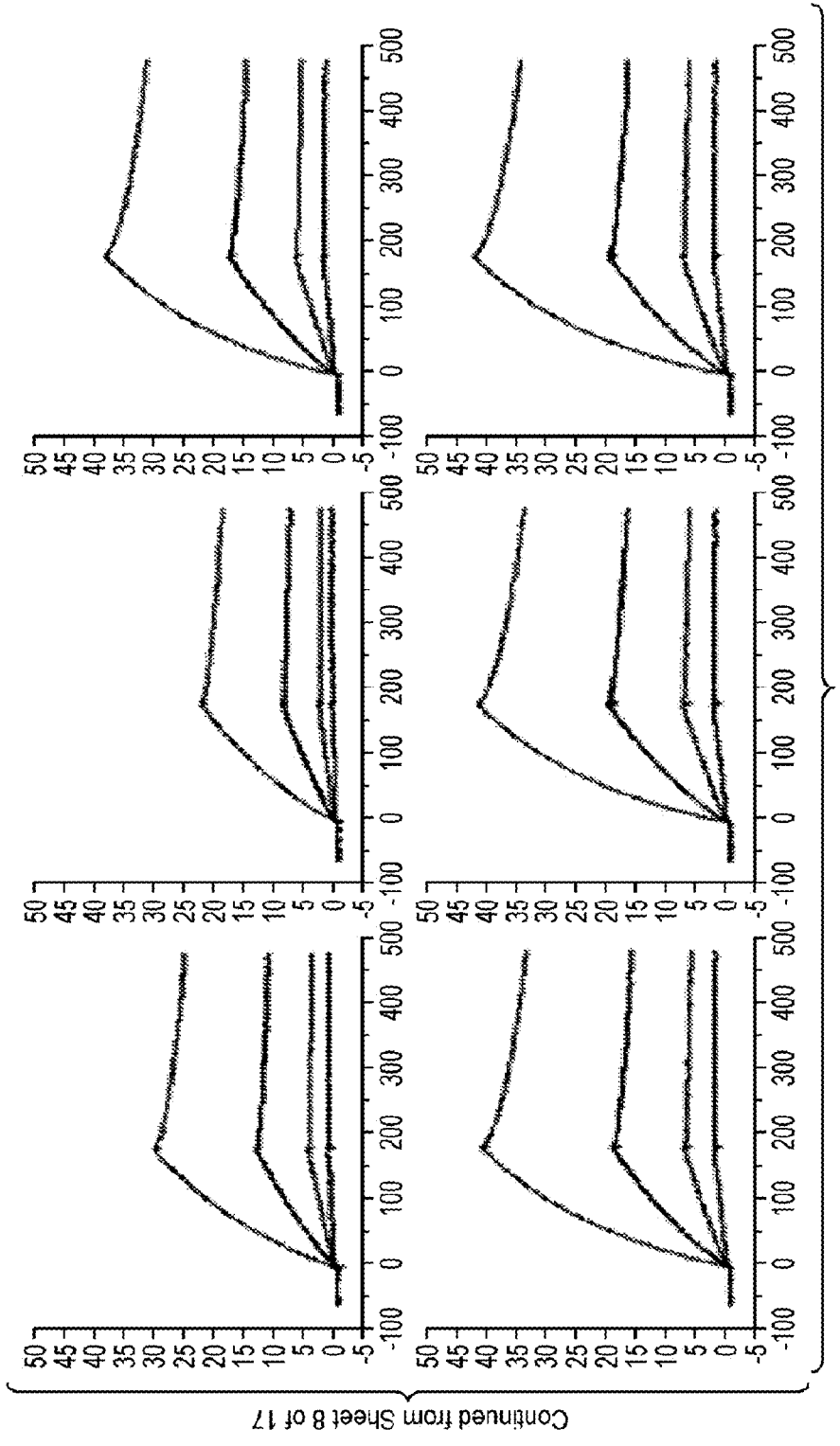
Figure 6:
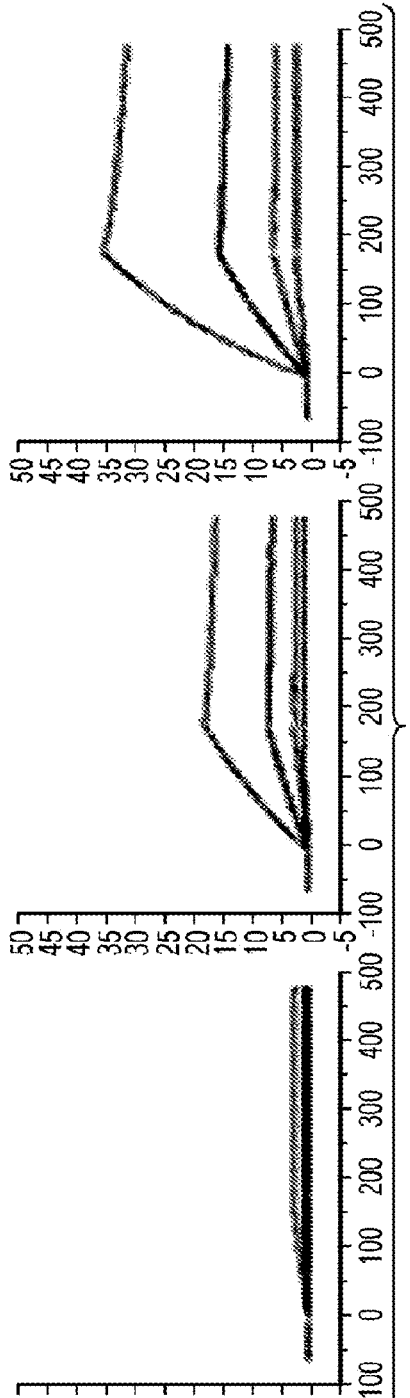
Figure 6:
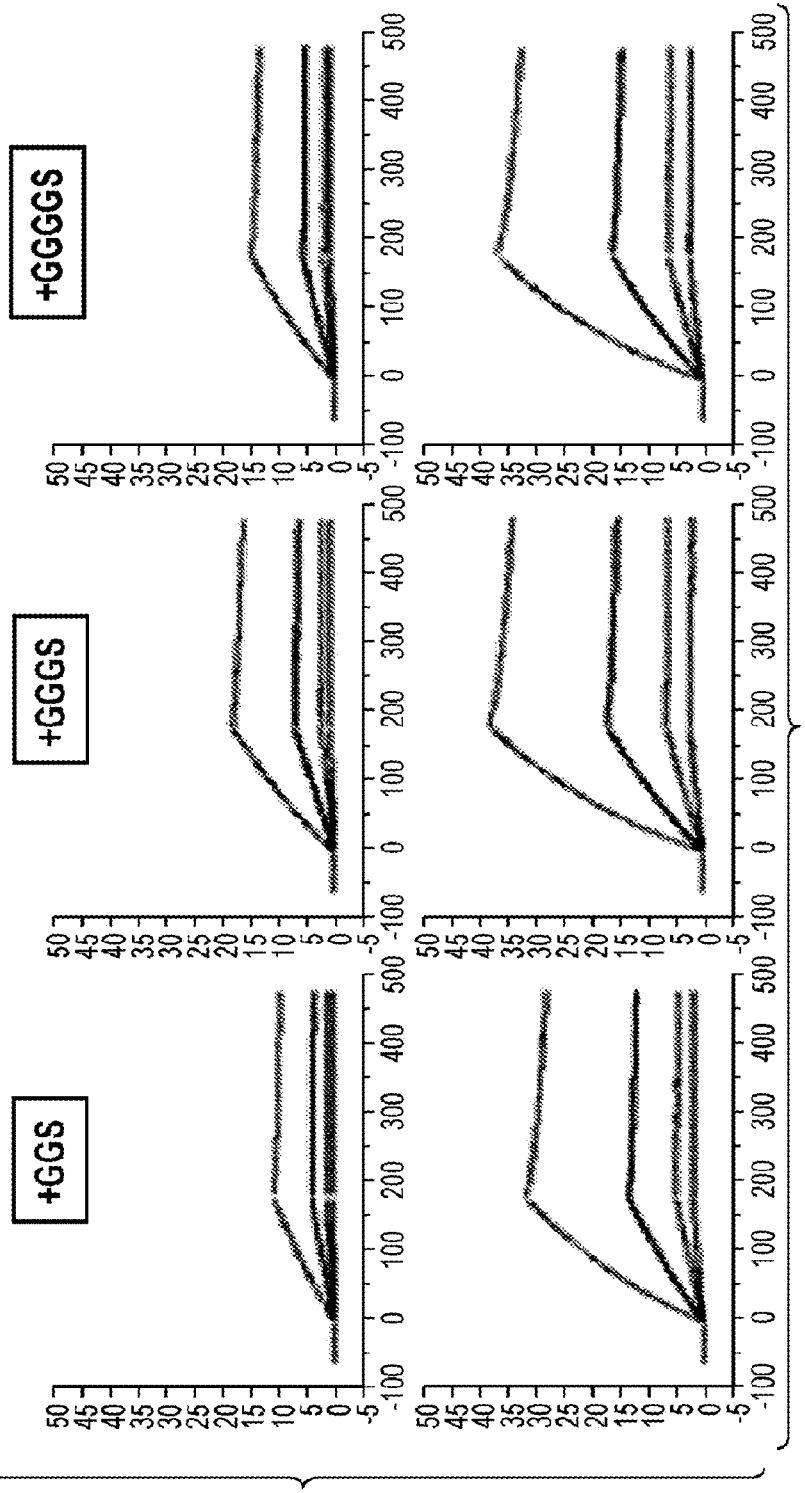
Figure 6:
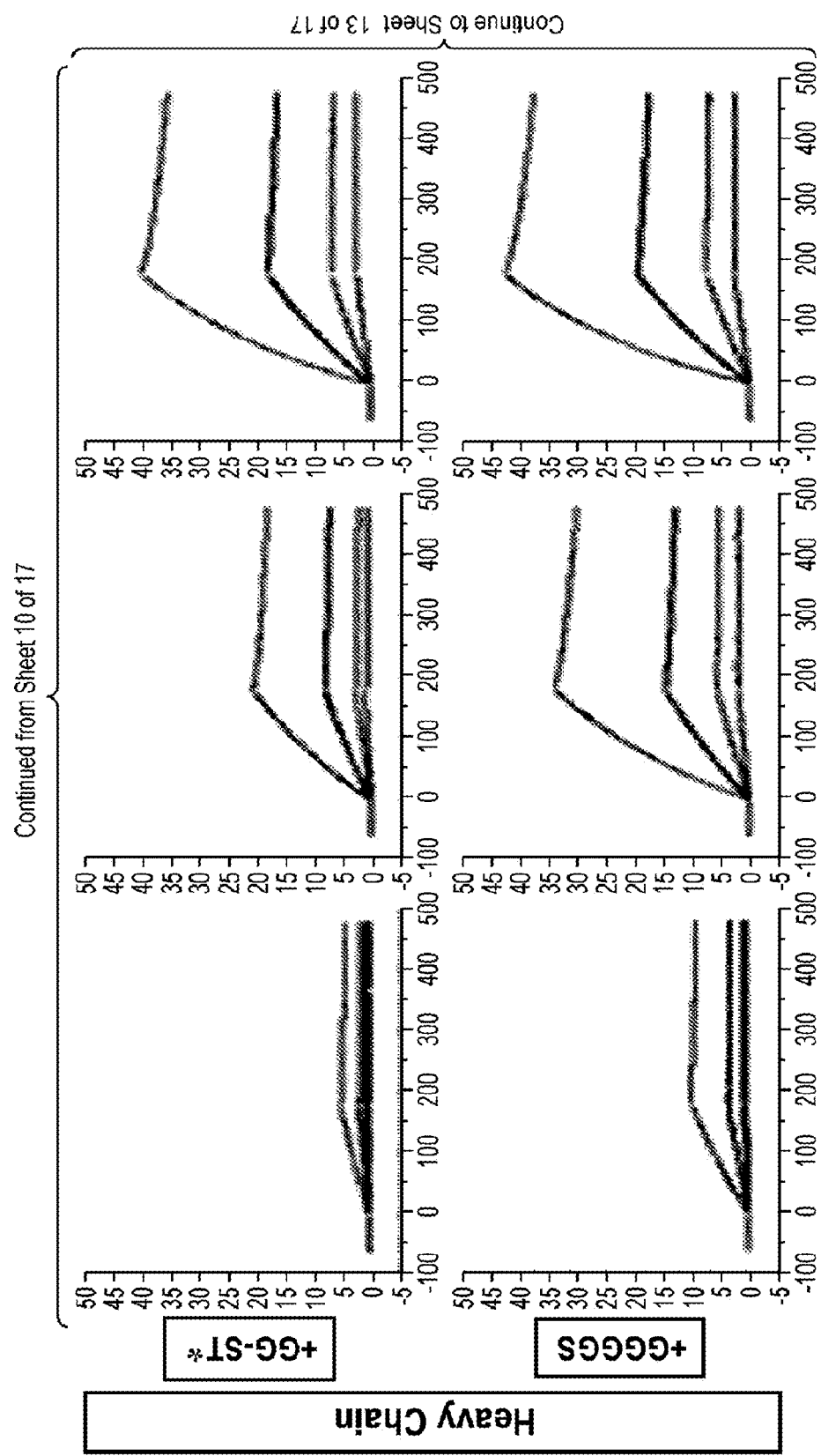
Figure 6:
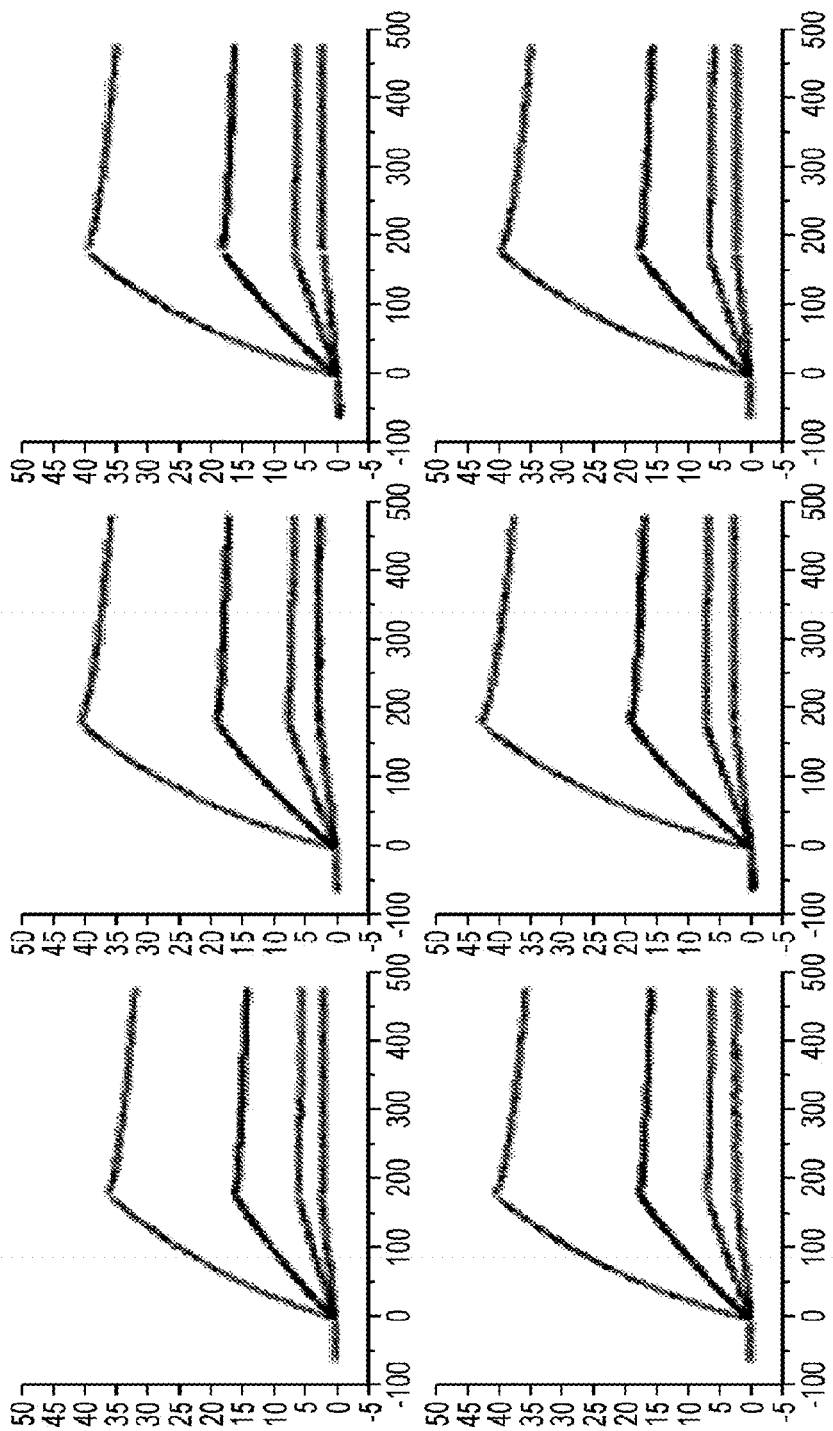

The Biacore T200 instrument was used to assess the TGFβ binding affinity of purified CAT192 WT and LC mutant Fabs. TGFβ1, TGFβ2, and TGFβ3 (124, 125, and 112 RU) were immobilized to a CM5 series S chip using amine chemistry. A wide concentration range was used to account for both the low and high affinity binders. The Fabs were diluted 3-fold from 270 to 0.37 nM in HBS-EP+ buffer. Each sample was injected in duplicate. The $K_D$ was determined using the typical concentration range with 30 nM as the top concentration. The Biacore binding results were in accordance with the Octet results described above, namely, addition of amino acids in the elbow region of CAT192 LC improved the binding affinity to TGFβ1. A step-wise improvement with insertion of each additional residue was demonstrated (FIG. 6). None of the CAT192 Fab LC mutants bound to TGFβ2 or TGFβ3 under the same conditions, demonstrating that the mutants retained the isoform-selectivity, while significantly increasing TGFβ1 binding. Therefore, the elbow engineered mutants were a set of novel variants with isoform-selectivity and high affinity binding to TGFβ1.

TABLE 3

$K_D$ of Modified Fabs

| Sample | $K_D$ (nM) |
|---|---|
| WT Fab | n/a |
| LC + G Fab | n/a |
| LC + GG Fab | 3.32 |
| LC + GGS Fab | 3.76 |
| A25S Fab | n/a |

Example 2: Modified IgG4 Antibody with Additional Amino Acids in the Heavy Chain Elbow Region As a follow up to the light chain mutants in the elbow region which has shown high affinity and TGFβ1-selective binding, mutants were also designed to increase flexibility/affinity by inserting additional amino acids in the heavy chain elbow region, which linked the antibody Fv domain to the CH1 domain. More specifically, mutants were designed to add one glycine (G), two glycines (GG), and four glycines and a serine (GGGGS; SEQ ID NO: 63) sequence into the wild-type heavy chain elbow region as shown below in Table 4, with the added amino acids underlined.

The HC+GG-ST was an unexpected by-product from the PCR mutagenesis process, which added the two glycines in the elbow as designed but also had two amino acids deleted at the end of the elbow region, as confirmed by DNA sequencing. This mutant had the same number of amino acids in the heavy chain elbow region but different amino acids composition in the elbow linker. It was included as a control for characterization and affinity comparisons.

CAT192 HC + G primers
Forward
(SEQ ID No. 50)
5'-ccaccgtgacagtgtctggcagcgccagc-3'

Complement
(SEQ ID No. 51)
5'-gctggcgctgccagacactgtcacggtgg-3'

CAT192 HC + GG-ST primers
Forward
(SEQ ID No. 52)
5'-ccaccgtgacagtgtctggcggcagcgccagc-3'

Complement
(SEQ ID No. 53)
5'-gctggcgctgccgccagacactgtcacggtgg-3'

CAT192 HC + GGGGS primers
Forward
(SEQ ID No. 54)
5'-caccaccgtgacagtgtctggcggcggcggcagcagcgccagca-3'

Complement
(SEQ ID No. 55)
5'-tgctggcgctgctgccgccgccgccagacactgtcacggtggtg-3'

CAT192 HC + GG primers
Forward
(SEQ ID NO: 59)
5'-caccaccgtgacagtgtctggcggcagcgccagca-3'

Complement
(SEQ ID No. 60)
5'-tgctggcgctgccgccagacactgtcacggtggtg-3'

These CAT192 HC mutants were co-expressed with CAT192 LC Fab using the Expi293F transfection system (Life Technologies) in a 24-well plate format (4×1 mL). Conditioned media was harvested 4 days post-transfection and then purified using PureSpeed IMAC tips from Rainin in order to accurately assess the affinity to TGFβ1.

TABLE 4

Modified-IgG4 Heavy Chain Elbow Insertion Mutants

| Name | Position | Amino acid sequence |
|---|---|---|
| WT | Heavy chain elbow region | TVTVSSAS (SEQ ID No. 44) |
| HC + G | Heavy chain elbow region | TVTVSGSAS (SEQ ID No. 45) |
| HC + GG | Heavy chain elbow region | TVTVSGGSAS (SEQ ID No. 46) |
| HC + GG-ST | Heavy chain elbow region | TVTVSGGSA (SEQ ID No. 47) |
| HC + GGGGS | Heavy chain elbow region | TVTVSGGGGSSAS (SEQ ID No. 48) |

The Biacore T200 instrument was used to assess the TGFβ binding affinity of purified CAT192 mutant Fabs as described in Example 1. The results shown in FIG. 6 suggested that, like the mutants in the light chain elbow region, addition of amino acids in the elbow region of CAT192 heavy chain also improved the binding affinity to TGFβ1. For example, the CAT192 HC+GGGGS (SEQ ID NO: 63) mutant showed very high affinity binding to TGFβ1.

Example 3: Heavy and Light Chain Combination Mutants

Combination CAT192 mutants were created by co-transfection DNAs harboring mutants at the elbow regions of both heavy and light chains using the Expi293F transfection system (Life Technologies) in a 24-well plate format (4×1 mL). The different combinations are listed in Table 5.

TABLE 5

Various Heavy and Light Chain Combination Mutants

| WT HC<br>WT LC | WT HC<br>LC + G | WT HC<br>LC + GG | WT HC<br>LC + GGS | WT HC<br>LC + GGGS<br>(SEQ ID<br>NO: 62) | WT HC<br>LC + GGGGS<br>(SEQ ID<br>NO: 63) |
|---|---|---|---|---|---|
| HC + G<br>WT LC | HC + G<br>LC + G | HC + G<br>LC + GG | HC + G<br>LC + GGS | HC + G<br>LC + GGGS<br>(SEQ ID<br>NO: 62) | HC + G<br>LC + GGGGS<br>(SEQ ID<br>NO: 63) |
| HC + GG<br>WT LC | HC + GG<br>LC + G | HC + GG<br>LC + GG | HC + GG<br>LC + GGS | HC + GG<br>LC + GGGS<br>(SEQ ID<br>NO: 62) | HC + GG<br>LC + GGGGS<br>(SEQ ID<br>NO: 63) |
| HC + GG-ST<br>WT LC | HC + GG-ST<br>LC + G | HC + GG-ST<br>LC + GG | HC + GG-ST<br>LC + GGS | HC + GG-ST<br>LC + GGGS<br>(SEQ ID<br>NO: 62) | HC + GG-ST<br>LC + GGGGS<br>(SEQ ID<br>NO: 63) |
| HC + GGGGS<br>(SEQ ID<br>NO: 63)<br>WT LC | HC + GGGGS<br>(SEQ ID<br>NO: 63)<br>LC + G | HC + GGGGS<br>(SEQ ID<br>NO: 63)<br>LC + GG | HC + GGGGS<br>(SEQ ID<br>NO: 63)<br>LC + GGS | HC + GGGGS<br>(SEQ ID<br>NO: 63)<br>LC + GGGS<br>(SEQ ID<br>NO: 62) | HC + GGGGS<br>(SEQ ID<br>NO: 63)<br>LC + GGGGS<br>(SEQ ID<br>NO: 63) |

Figure 3:
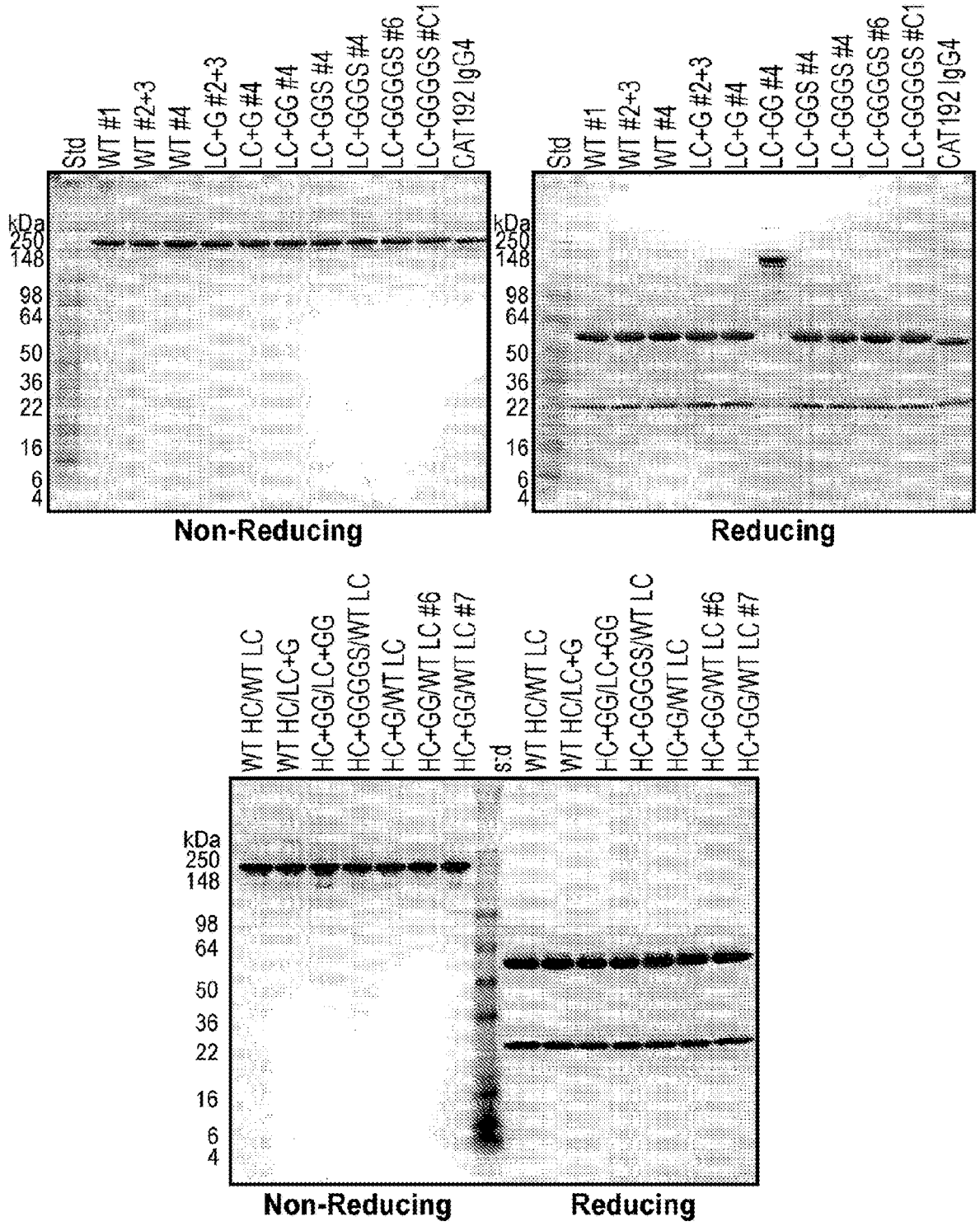
FIG. 3 shows the results of an SDS-PAGE gel of purified IgG variants with additional amino acids in the heavy and light chain elbow regions. The SDS-PAGE shows the purity of the purified IgG variants under reducing and non-reducing conditions.

Conditioned media was harvested 4 days post-transfection and then purified using PureSpeed IMAC tips from Rainin in order to accurately assess the affinity to TGFβ1. The Biacore T200 instrument was used to assess the TGFβ binding affinity of purified CAT192 mutant Fabs as described in Example 1. The results shown in FIG. 3 suggested that the combination mutants restored the high affinity binding to TGFβ1 of CAT192. The binding affinity (KD) by these mutant Fabs are listed in Table 6.

TABLE 6

TGFβ1-Binding Affinity (KD) of the Heavy and Light Chain Combination Mutants Determined by Biacore

| Fabs | Antigen | $k_a$ (×10⁵/Ms) | $k_d$ (×10⁻⁴/s) | $K_D$ nM |
|---|---|---|---|---|
| WT HC/WT LC | TGFβ1 | n/d | n/d | >100 |
| WT HC/LC + G | TGFβ1 | 0.16 | 10.6 | 66.5 |
| WT HC/LC + GG | TGFβ1 | 0.70 | 5.69 | 8.1 |
| WT HC/LC + GGS | TGFβ1 | 0.68 | 5.95 | 8.8 |
| WT HC/LC + GGGS (SEQ ID NO: 62) | TGFβ1 | 0.89 | 5.87 | 6.6 |
| WT HC/LC + GGGGS (SEQ ID NO: 63) | TGFβ1 | 1.18 | 5.83 | 5.0 |
| HC + G/WT LC | TGFβ1 | n/d | n/d | n/d |
| HC + G/LC + G | TGFβ1 | 1.51 | 6.32 | 4.2 |
| HC + G/LC + GG | TGFβ1 | 2.36 | 6.64 | 2.8 |
| HC + G/LC + GGS | TGFβ1 | 2.27 | 6.96 | 3.1 |

TABLE 6-continued

TGFβ1-Binding Affinity (KD) of the Heavy and Light Chain
Combination Mutants Determined by Biacore

| Fabs | Antigen | $k_a$ (×10⁵/Ms) | $k_d$ (×10⁻⁴/s) | $K_D$ nM) |
|---|---|---|---|---|
| HC + G/LC + GGGS (SEQ ID NO: 62) | TGFβ1 | 2.54 | 6.93 | 2.7 |
| HC + G/LC + GGGGS (SEQ ID NO: 63) | TGFβ1 | 2.62 | 6.90 | 2.6 |
| HC + GG/WT LC | TGFβ1 | 0.2 | 5.3 | 31.7 |
| HC + GG/LC + G | TGFβ1 | 1.1 | 4.9 | 4.4 |
| HC + GG/LC + GG | TGFβ1 | 2.2 | 3.8 | 1.8 |
| HC + GG/LC + GGS | TGFβ1 | 1.8 | 4.3 | 2.3 |
| HC + GG/LC + GGGS (SEQ ID NO: 62) | TGFβ1 | 2.4 | 3.7 | 1.5 |
| HC + GG/LC + GGGGS (SEQ ID NO: 63) | TGFβ1 | 2.2 | 3.9 | 1.8 |
| HC + GG-ST/WT LC | TGFβ1 | 0.85 | 8.11 | 9.6 |
| HC + GG-ST/LC + G | TGFβ1 | 1.31 | 5.87 | 4.5 |
| HC + GG-ST/LC + GG | TGFβ1 | 2.04 | 6.64 | 3.3 |
| HC + GG-ST/LC + GGS | TGFβ1 | 2.11 | 6.67 | 3.2 |
| HC + GG-ST/LC + GGGS | TGFβ1 | 1.47 | 6.31 | 4.3 |
| HC + GG-ST/LC + GGGGS (SEQ ID NO: 63) | TGFβ1 | 2.50 | 7.17 | 2.9 |
| HC + GGGGS (SEQ ID NO: 63) WT LC | TGFβ1 | 0.68 | 5.79 | 8.5 |
| HC + GGGGS (SEQ ID NO: 63)/LC + G | TGFβ1 | 2.21 | 6.77 | 3.1 |
| HC + GGGGS (SEQ ID NO: 63)/LC + GG | TGFβ1 | 2.65 | 7.27 | 2.7 |
| HC + GGGGS (SEQ ID NO: 63)/LC + GGS | TGFβ1 | 2.63 | 7.09 | 2.7 |
| HC + GGGGS (SEQ ID NO: 63)/LC + GGGS | TGFβ1 | 2.78 | 7.16 | 2.6 |
| HC + GGGGS (SEQ ID NO: 63)/LC + GGGGS (SEQ ID NO: 63) | TGFβ1 | 2.64 | 7.44 | 2.8 |
| GC1008 Fab | TGFβ1 | 7.11 | 20.80 | 2.9 | n/d = none detected

Fewer amino acids insertions were required when the elbow region of both heavy chain and light chain were engineered. For example, combination of "HC+G" and "LC+G" mutant showed very high affinity binding to TGFβ1.

Example 4: Affinity and Potency Characterization of Full Length IgG4 Variants

Mutants in IgG4 format were generated to determine if the regained affinity by Biacore can be confirmed in the A549 cell-based potency assay. The CAT192 HC Fab was cloned into the heavy chain S228P IgG4 backbone to minimize the half-antibody formation, and Expi293F cells were then co-transfected with CAT192 IgG4 S228P HC and the LC insertion mutant.

Figure 4:
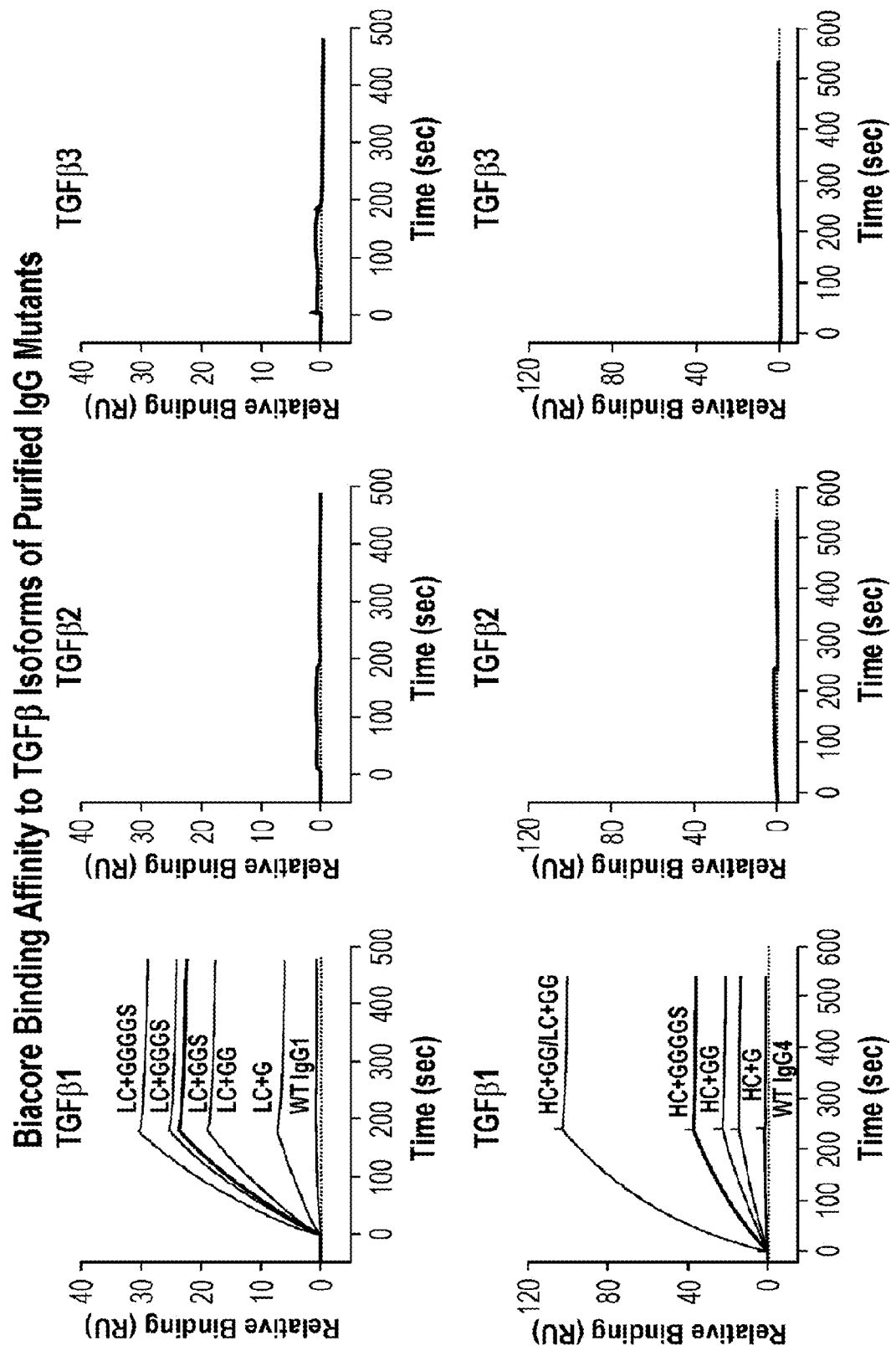
FIG. 4 shows a Biacore binding assay of purified IgG variants with additional amino acids in the heavy and light chain elbow regions. The Biacore assay result demonstrates the isoform-selective and high affinity binding by the variants.

A 30 mL transfection was performed on the full length CAT192 HC and LC insertion mutants in order to obtain enough material for the bioassay. Expi293F cells were transfected with 30 μg DNA (15 μg LC+15 μg HC). Conditioned media was collected 4 days after the transfection and analyzed by Octet using Protein A biosensors to have around 200 μg/mL expression. The CM was then purified using Hi-Trap Protein A HP columns with a peristaltic pump. CM was loaded onto each column at 0.5 mL/min, washed with 25 column volumes (CV) of 50 mM NaPi, 25 mM NaCl pH 7.1 (2 mL/min), washed with 25 CV of 10 mM sodium succinate pH 6.0 (2 mL/min), and eluted in 3×2 mL fractions with 10 mM sodium succinate pH 3.75 at 1 mL/min (labeled #1, #2, #3). The protein A eluates were neutralized with 0.2 M NaOH, and 0.2 M NaCl was added for a final concentration of 40 mM NaCl. The samples were then concentrated and buffer exchanged into 50 mM NaPi, 25 mM NaCl pH 7.1. These CAT192 IgG4 S228P HC and LC insertion mutant protein A eluates were then run on a 4-20% Tris Glycine gel (FIG. 3) and compared by Biacore for TGFβ1/TGFβ2/TGFβ3 binding (FIG. 4). Biacore results showed that the purified CAT192 IgG4 mutants indeed regained TGFβ1 binding. None of the mutants bound to TGFβ2 or TGFβ3 (FIG. 4).

A 150 mL transfection was performed on the CAT192 HC and LC Fab insertion mutants to obtain enough material for the structure studies. Expi293F cells were transfected with 150 μg DNA (75 μg LC+75 μg HC). Conditioned media was collected 5 days after the transfection. The CM was then purified using His-Trap Excel columns equilibrated with 20 mM NaPi pH 7.4, 500 mM NaCl, 5 mM imidazole. Fab protein was eluted with 20 mM NaPi pH 7.4, 500 mM NaCl, 500 mM imidazole and immediately buffer exchanged into

TABLE 7

TGFβ1-Binding Affinity (KD) of the Full-length IgG4 Variants as Determined by Biacore

| Sample | $k_a$ (×10$^5$/Ms) | $k_d$ (×10$^{-4}$/s) | $K_D$ (nM) |
|---|---|---|---|
| CAT192 IgG4 S228P | n/d | n/d | >100 |
| CAT192 IgG4 S228P LC + G | 0.15 | 5.26 | 36.1 |
| CAT192 IgG4 S228P LC + GG | 1.0 | 0.2 | 0.2 |
| CAT192 IgG4 S228P LC + GGS | 0.8 | 2.2 | 2.7 |
| CAT192 IgG4 S228P LC + GGGS (SEQ ID NO: 62) | 0.6 | 0.6 | 1.0 |
| CAT192 IgG4 S228P LC + GGGGS (SEQ ID NO: 63)) | 0.6 | 1.5 | 2.6 |
| CAT192 IgG4 S228P HC + G | 0.5 | 2.1 | 4.1 |
| CAT192 IgG4 S228P HC + GG | 1.0 | 2.0 | 2.2 |
| CAT192 IgG4 S228P HC + GGGGS (SEQ ID NO: 63) | 1.1 | 1.5 | 1.3 |
| CAT192 IgG4 S228P HC + GG/LC + GG | 2.4 | 0.5 | 0.2 | n/d = none detected

Figure 5:
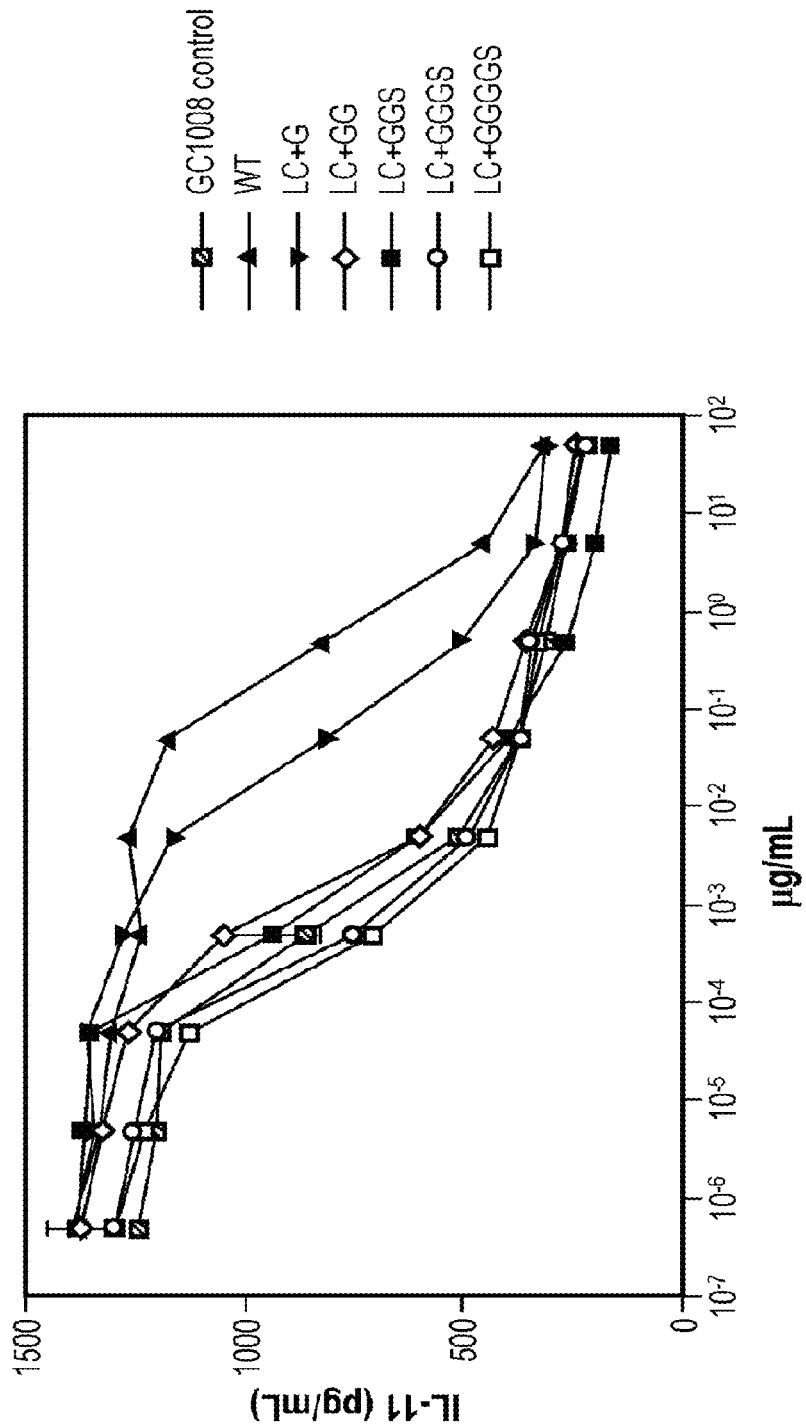
FIG. 5 shows an A549 cell bioassay of purified IgG variants with additional amino acids in the light chain elbow regions. The A549 assay compares the inhibitory effects by various antibody constructs on TGFβ1-stimulated IL-11 production, showing the elbow engineered variants are highly potent in this cell-based potency assay.

The CAT192 IgG S228P LC insertion mutants were then characterized in a A549 cell potency assay (Rapoza et al., 2006, J Immunol Methods, Vol 316, pp 18). The results (FIG. 5) showed that the CAT192 insertion mutants neutralized TGFβ1 activity, as demonstrated by the inhibitory effects by the mutants on TGFβ1-stimulated IL-11 production. It appeared that two glycines added to the light chain elbow were sufficient to for CAT192 to regain efficacy, as observed in the Biacore binding experiment.

Example 5: Thermostability Study

Figure 7:
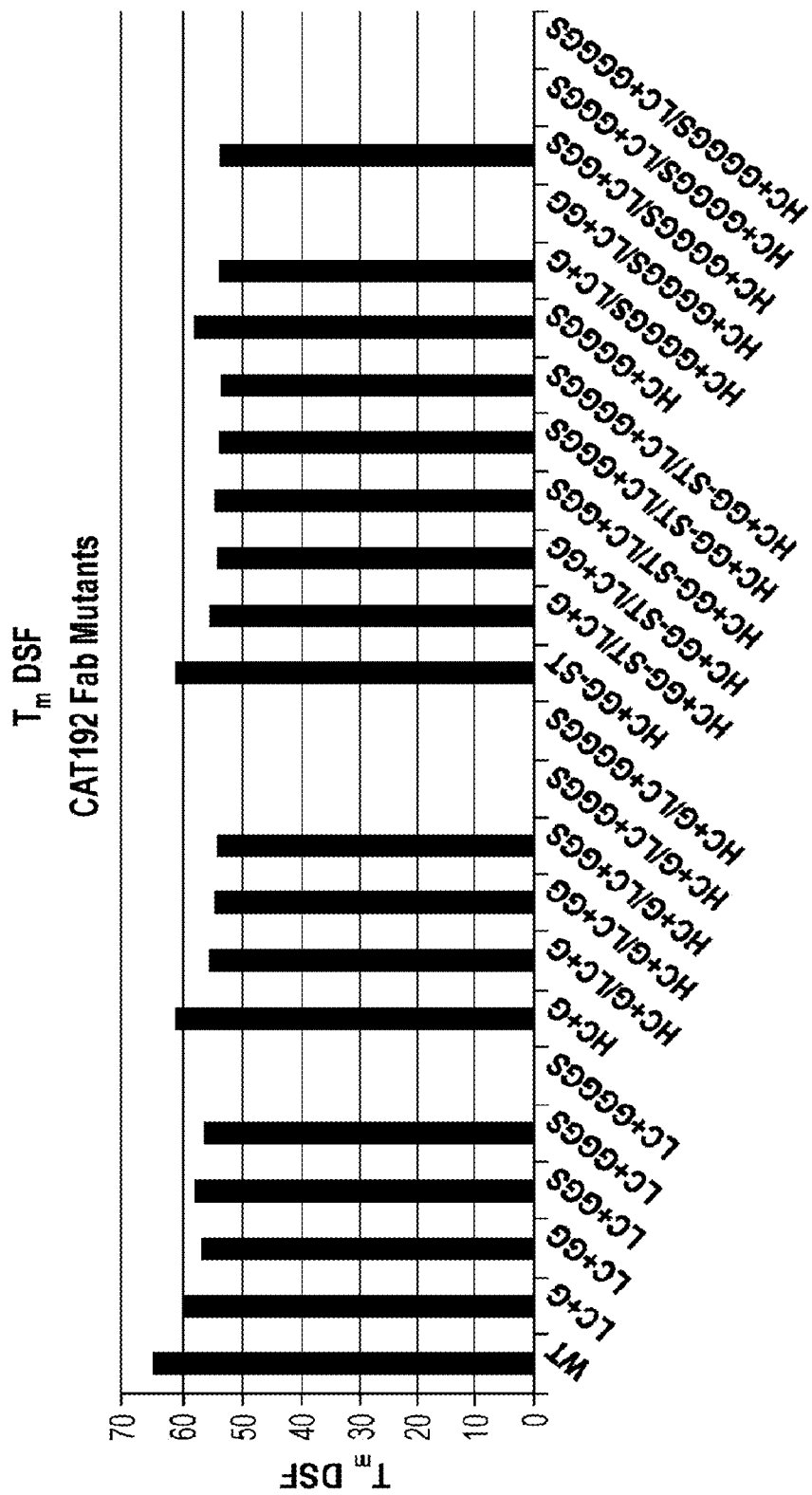
FIG. 7 shows results of a Differential Scanning Fluorimetry (DSF) analysis of the thermostability of the CAT192 Fab mutants.
Figure 8:
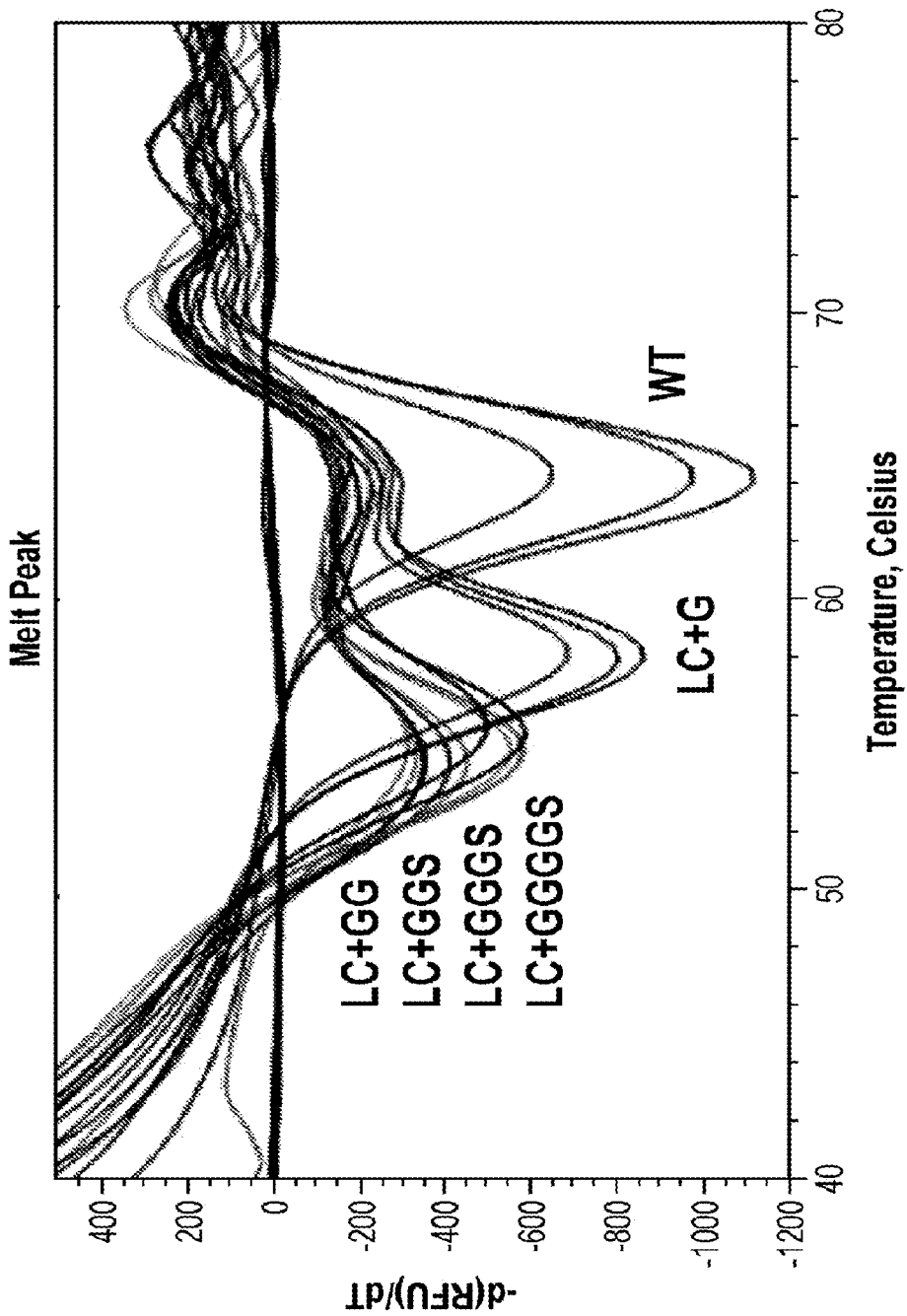
FIG. 8 shows results of a Differential Scanning Fluorimetry (DSF) analysis of the thermostability of the CAT192 IgG4 mutants.

Differential Scanning Fluorimetry (DSF) was performed on the elbow-insertion mutants to determine how the additional amino acids at the hinge region of heavy chain and light chain affected the thermostability of the CAT192 Fab insertion mutants. The basic principle of DSF is that as the temperature increases, a fluorescent dye binds to the hydrophobic regions of the protein as it unfolds providing an increase in signal. This method can be performed with limited sample and can be used to get relative stability of samples in a high throughput manner. Sypro orange was used as the fluorescent dye. The conditions used were 0.1 mg/mL protein, a 1:4000 dye ratio and a total volume of 10 μL. The results showed that relative stability of the CAT192 Fab insertion mutants decreased slightly with the addition of glycines in the elbow, with the least stable mutants having the longest addition (FIG. 7). The Tm values are summarized in FIG. 7. The Tm values of some of the longer chain mutants were not calculated due to their unfolding pattern. The slight decrease was also observed when some of the light chain mutants were converted from Fab into IgG4 format (FIG. 8).

Example 6: Crystal Structure Determination of CAT192 Fab Variants

The protein structures of CAT192 Fab WT and 3 variants were solved to provide the structural explanation as to how the high affinity was restored with the increased flexibility of the variable domains.

20 mM HEPES pH 7.0, 50 mM NaCl using a size exclusion chromatography column (Superdex 200 10/300). The Fabs were then concentrated to 20 mg/mL and sparse matrix screens were set-up at both room temperature and 4° C. All crystals used for structure determination were obtained at 4° C. in a 1:1 protein to crystallization condition ratio. Wild-type protein and the lower binding affinity mutants crystallized in a P21 space group in similar PEG conditions (WT: 12% PEG 8K/0.1 M sodium cacodylate pH 6/0.2 M MgCl$_2$, CAT192 WT HC/LC+G: 12% PEG 20K/0.1 M MES pH 6.5, CAT192 HC+GGGGS (SEQ ID NO: 63)/WT LC: 12% PEG 20K, 0.1 M MES pH 5.75). The high binding affinity mutant (HC+GG/LC+GG) crystallized in 2 M ammonium sulfate, 0.1 M sodium acetate pH 4.6 (space group: C2).

Figure 9:
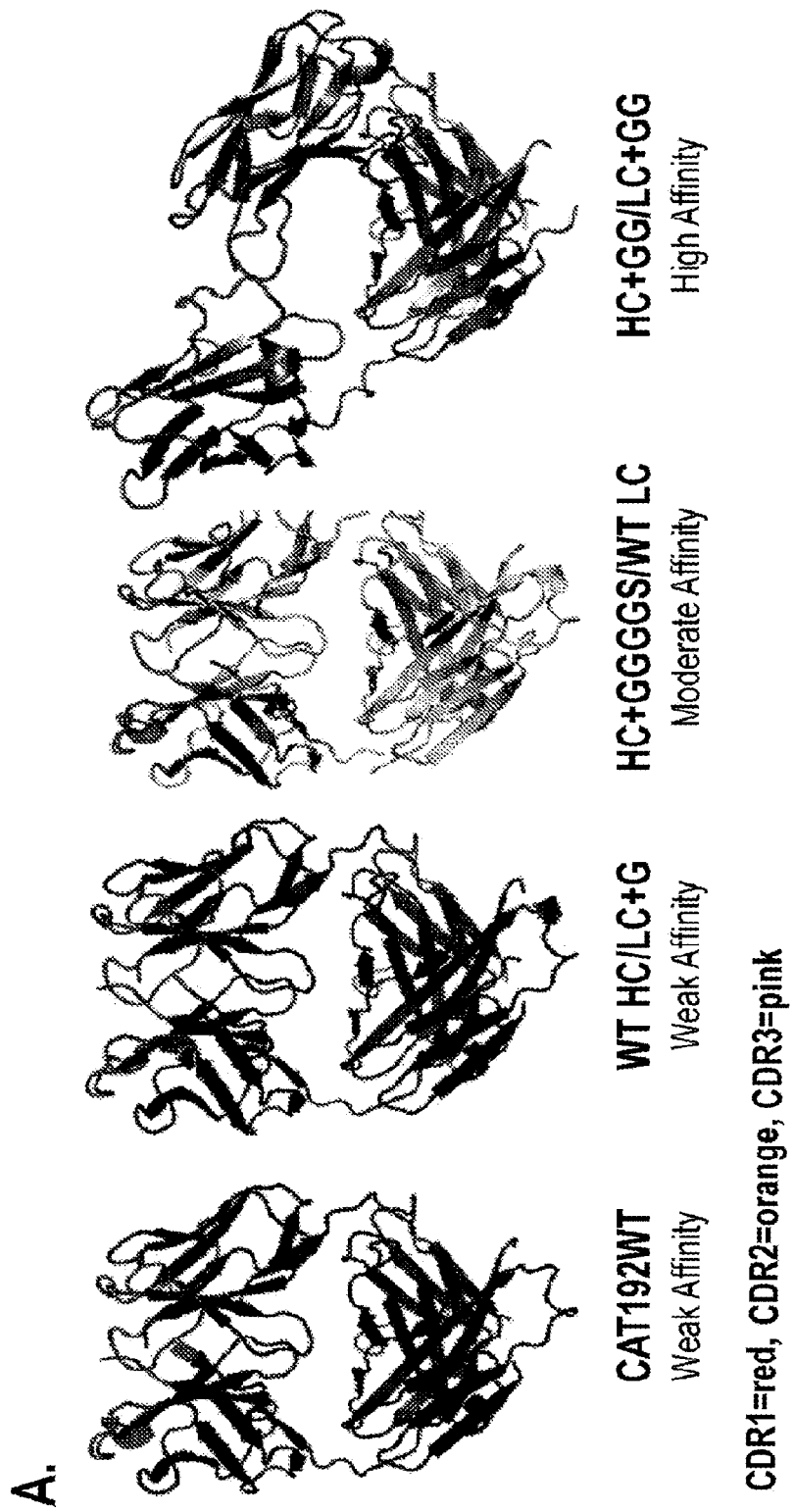
FIG. 9 shows the crystal structures solved for the CAT192 Fab variants.
Figure 9:
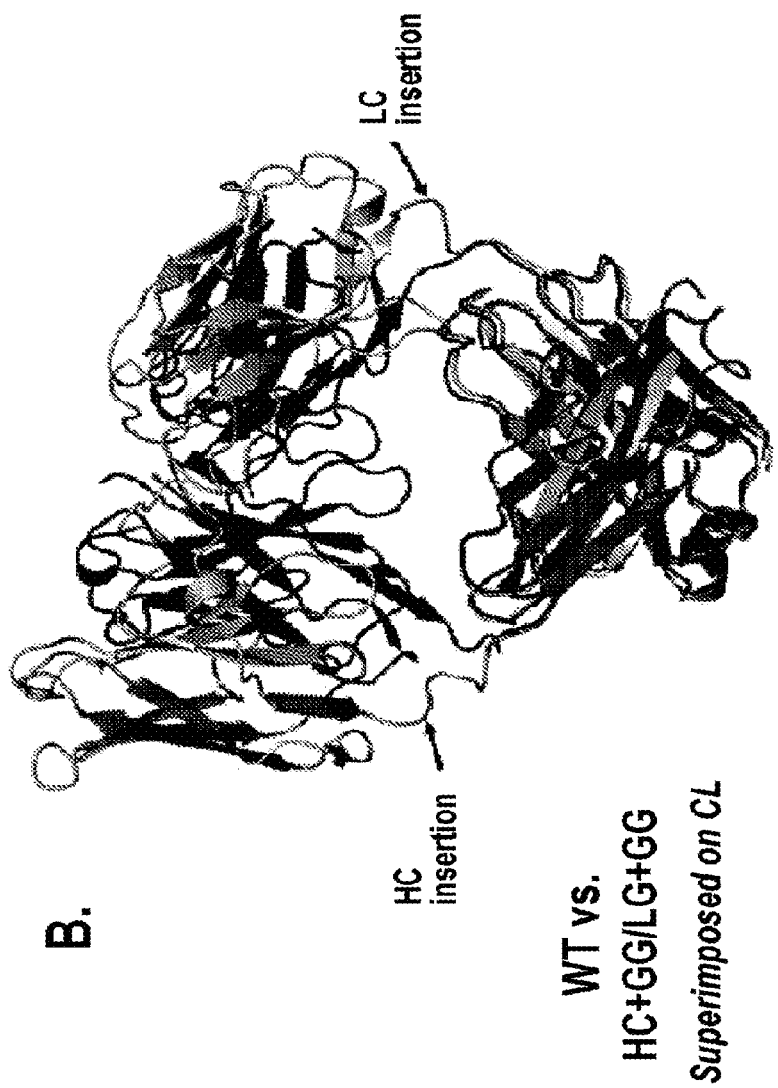

The low/moderate binding affinity variants and the wild type Fab structures (HC+WT/LC+G and HC+GGGGS (SEQ ID NO: 63)/LC+WT) were nearly identical (FIG. 9, part A). WT HC/LC+G and HC+GGGGS (SEQ ID NO: 63)/WT LC superimposed with WT CAT192 with a R.M.S.D of 0.516 Å and 0.538 Å respectively. In each of these structures, the electron density for the CDRH3 region was missing for all molecules in the asymmetric unit. This implied that this CDR was highly flexible for the low/moderate binding affinity mutants. In contrast, the high binding affinity mutant (HC+GG/LC+GG) displayed large conformational changes in the variable domains compared to the other CAT192 Fab structures (FIG. 9, part A). While the constant domains between all four Fabs superimposed nicely, the variable domains in CAT192 HC+GG/LC+GG shifted significantly compared to the other structures (FIG. 9, part B). Furthermore, the HC CDR3 region was completely structured in the high binding affinity structure and was stabilized by interacting with the LC CDR3 (<3 Å). These four structures, in accordance with the Biacore results, suggested that large conformational rearrangement was required to restore the high binding affinity of CAT192.

SEQUENCE LISTING
SEQ ID No. 1: Human IgG1 VH domain Clone SL15 (SQN4 U.S. Pat. No. 6,492,497)
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSS

SEQ ID No. 2: Human IgG1 VH domain Clone JT182 (SQN10 U.S. Pat. No. 6,492,497)
QVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTPASPDWGQGTTVTVSS

SEQ ID No. 3: Human IgGI Vκ domain Clone SL15A: (SQN6 U.S. Pat. No. 6,492,497)
EIVLTQSPSSLSASVGDRVTITCRASQGIGDDLGWYQQKPGKAPILLTYGTSTL

QSGVPSRFSGSGSGTDFTLTINSLQPEDFATYYCLQDSNYPLTFGGGTRLEIK

SEQ ID No. 4: Human IgGI Vκ domain Clone SL15S: (SQN8 U.S. Pat. No. 6,492,497)
EIVLTQSPSSLSASVGDRVTITCRSSQGIGDDLGWYQQKPGKAPILLTYGTSTL

QSGVPSRFSGSGSGTDFTLTINSLQPEDFATYYCLQDSNYPLTFGGGTRLEIK

SEQ ID No. 5: Human IgG1 Hinge Region
PKSCDKTHTCPPCPAPELLGGP

SEQ ID No. 6: Human IgG1 Fc Region
SVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

SEQ ID No. 7
SYGMH

SEQ ID No. 8
VISYDGSIKYYADSVKG

SEQ ID No. 9
TGEYSGYDTSGVEL

SEQ ID No. 10
TGEYSGYDTDPQYS

SEQ ID No. 11
TGFYSGYDTPASPD

SEQ ID No. 12
RASQGIGDDLG

SEQ ID No. 13
GTSTLQS

SEQ ID No. 14
LQDSNYPLT

SEQ ID No. 15
TGX$_1$YSGYDTX$_2$X$_3$X$_4$X$_5$X$_6$

SEQ ID No. 16: CAT192 (IgG4) Light Chain
EWLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKR

TVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGE

C

SEQ ID No. 17: CAT192 (IgG4) Heavy Chain
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTCNVD

HKPSNTKVDKRVESKYGPPCPSCPAPEFLGGPSVFLFPPKPKDTLMISRTPEVT

CVVVDVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVDKSR

WQEGNVFSCSVMHEALHNHYTQKSLSLSLGK

SEQ ID No. 18: CAT192 (IgG4) S228P Heavy Chain
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTCNVD

HKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVDKSR

WQEGNVFSCSVMHEALHNHYTQKSLSLSLGK

SEQ ID No. 19: CAT191 (scFv)
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSSSGGGSGGGGSGGGGSEIVLTQSPSSLSASVGD

RVTITCRSSQGIGDDLGWYQQKPGKAPILLIYGTSTLQSGVPSRFSGSGSGTDF

TLTINSLQPEDFATYYCLQDSNYPLTFGGGTRLEIK

SEQ ID No. 20: Human TGFβ1
ALDTNYCFSSTEKNCCVRQLYIDFRKDLGWKWIHEPKGYHANFCLGPCPYIW

SLDTQYSKVLALYNQHNPGASAAPCCVPQALEPLPIVYYVGRKPKVEQLSNM

IVRSCKCS

SEQ ID No. 21: CAT192 IgG4 Wild-type LC Elbow Region
LEIKRTVA

SEQ ID No. 22: Mutant LC Elbow Region with 1 Additional Amino Acid Inserted
LEIKGRTVA SEQ ID No. 23: Mutant LC Elbow Region with 2 Additional Amino Acids Inserted
LEIKGGRTVA SEQ ID No. 24: Mutant LC Elbow Region with 3 Additional Amino Acids Inserted
LEIKGGSRTVA SEQ ID No. 25: Mutant LC Elbow Region with 4 Additional Amino Acids Inserted
LEIKGGGSRTVA SEQ ID No. 26: Mutant LC Elbow Region with 5 Additional Amino Acids Inserted
LEIKGGGGSRTVA SEQ ID No. 27: Coding sequence of CAT192 (IgG1) Light Chain
atgggctggtcctgcatcatcctgtttctggtggccacagccaccggcgtgcacagcGAGATCGTGCTGACA

CAGAGCCCCAGCAGCCTGTCTGCCAGCGTGGGCGACAGAGTGACCATCAC

CTGTAGAGCCAGCCAGGGCATCGGCGACGACCTGGGATGGTATCAGCAGA

AGCCTGGCAAGGCCCCCATCCTGCTGATCTACGGCACCAGCACACTGCAG

```
AGCGGCGTGCCCTCCAGATTTTCTGGCAGCGGCTCCGGCACCGACTTCACC

CTGACCATCAACAGCCTGCAGCCCGAGGACTTCGCCACCTACTACTGTCTG

CAAGACAGCAACTACCCCCTGACCTTCGGCGGAGGCACCCGGCTGGAAAT

CAAGCGTACGGTGGCCGCTCCTTCCGTGTTCATCTTCCCTCCCTCCGACGA

GCAGCTGAAGTCCGGCACCGCCTCCGTGGTGTGTCTGCTGAACAACTTCTA

CCCTCGGGAGGCCAAGGTGCAGTGGAAGGTGGACAACGCCCTGCAGTCCG

GCAACTCCCAGGAGTCCGTCACCGAGCAGGACTCCAAGGACAGCACCTAC

TCCCTGTCCTCCACCCTGACCCTGTCCAAGGCCGACTACGAGAAGCACAA

GGTGTACGCCTGTGAGGTGACCCACCAGGGCCTGTCCAGCCCTGTGACCA

AGTCCTTCAACCGGGGCGAGTGCTGA
```

SEQ ID No. 28: CAT192LC + G (LEIK*G*RTVA), Forward
5'-ggctggaaatcaagggccgtacggtggccgc-3'

SEQ ID No. 29: CAT192LC + G (LEIK*G*RTVA), Complement
5'-gcggccaccgtacggcccttgatttccagcc-3'

SEQ ID No. 30: CAT192LC + GG (LEIK*GG*RTVA), Forward
5'-ggctggaaatcaagggcggccgtacggtggccgc-3'

SEQ ID No. 31: CAT192LC + GG (LEIK*GG*RTVA), Complement
5'-gcggccaccgtacggccgcccttgatttccagcc-3'

SEQ ID No. 32: CAT192LC + GGS (LEIK*GGS*RTVA), Forward
5'-ggctggaaatcaagggcggcagccgtacggtggccgc-3'

SEQ ID No. 33: CAT192LC + GGS (LEIK*GGS*RTVA), Complement
5'-gcggccaccgtacggctgccgcccttgatttccagcc-3'

SEQ ID No. 34: CAT192LC + GGGS (LEIK*GGGS*RTVA), Forward
5'-ggctggaaatcaagggcggcggcagccgtacggtggccgc-3'

SEQ ID No. 35: CAT192LC + GGGS (LEIK*GGGS*RTVA), Complement
5'-gcggccaccgtacggctgccgccgcccttgatttccagcc-3'

SEQ ID No. 36: CAT192LC + GGGGS (LEIK*GGGGS*RTVA), Forward
5'-ggctggaaatcaagggcggcggcggcagccgtacggtggccgc-3'

SEQ ID No. 37: CAT192LC + GGGGS (LEIK*GGGGS*RTVA), Complement
5'-gcggccaccgtacggctgccgccgccgcccttgatttccagcc-3'

SEQ ID No. 38: CAT192 IgG1 Wild-Type LC
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKR

TVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGE

C

SEQ ID No. 39: Mutant Light Chain with 1 Additional Amino Acid Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIK*G*

RTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRG

EC

-continued

SEQ ID No. 40: Mutant Light Chain with 2 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

GRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNR

GEC

SEQ ID No. 41: Mutant Light Chain with 3 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

GSRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFN

RGEC

SEQ ID No. 42: Mutant Light Chain with 4 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

GGSRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSF

NRGEC

SEQ ID No. 43: Mutant Light Chain with 5 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

GGGSRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKS

FNRGEC

SEQ ID No. 44: CAT192 IgG4 Wild-Type HC Elbow Region
TVTVSSAS

SEQ ID No. 45: Mutant HC Elbow Region with 1 Additional Amino Acid
Inserted
TVTVSGSAS SEQ ID No. 46: Mutant HC Elbow Region with 2 Additional Amino Acids
Inserted
TVTVSGGSAS SEQ ID No. 47: Mutant HC Elbow Region with 2 Additional Amino Acids
Inserted and one Amino Acid Deleted
TVTVSGGSA SEQ ID No. 48: Mutant HC Elbow Region with 5 Additional Amino Acids
Inserted
TVTVSGGGGSSAS SEQ ID No. 49: Coding Sequence of CAT192 IgG4 Wild-Type HC
ATGGGCTGGTCCTGCATCATCCTGTTTCTGGTGGCCACCGCCACCGGCGTG

CACTCTGAAGTGCAGCTGGTGGAATCTGGCGGCGGAGTGGTGCAGCCTGG

CAGAAGCCTGAGACTGAGCTGTGCCGCCAGCGGCTTCACCTTCAGCAGCT

ACGGAATGCACTGGGTGCGCCAGGCCCCTGGCAAAGAACTGGAATGGGT

GGCCGTGATCAGCTACGACGGCAGCATCAAGTACTACGCCGACAGCGTGA

AGGGCCGGTTCACCATCTCCCGGGACAACAGCAAGAACACCCTGTACCTG

CAGATGAACAGCCTGCGGGCCGAGGACACCGCCGTGTACTACTGTGCTAG

AACCGGCGAGTACAGCGGCTACGACACCGACCCTCAGTACTCTTGGGGCC

```
AGGGCACCACCGTGACAGTGTCTAGCGCCAGCACCAAGGGCCCAAGCGTG

TTCCCTCTGGCCCCTTGCAGCAGAAGCACCAGCGAATCTACAGCCGCCCT

GGGCTGCCTCGTGAAGGACTACTTTCCCGAGCCCGTGACAGTGTCCTGGA

ACTCTGGCGCCCTGACCAGCGGAGTGCATACCTTTCCAGCCGTGCTGCAG

AGCAGCGGCCTGTACTCTCTGAGCAGCGTCGTGACTGTGCCCAGCAGCTC

TCTGGGCACCAAGACCTACACCTGTAACGTGGACCACAAGCCCAGCAACA

CCAAGGTGGACAAGAGAGTGCATCACCACCACCATCAC

SEQ ID No. 50: CAT192HC + G (TVTVSGSAS), Forward
5'-ccaccgtgacagtgtctggcagcgccagc-3'

SEQ ID No. 51: CAT192HC + G (TVTVSGSAS), Complement
5'-gctggcgctgccagacactgtcacggtgg-3'

SEQ ID No. 52: CAT192HC + GG-ST (TVTVSGGSA), Forward
5'-ccaccgtgacagtgtctggcggcagcgccagc-3'

SEQ ID No. 53: CAT192HC + GG-ST (TVTVSGGSA), Complement
5'-gctggcgctgccgccagacactgtcacggtgg-3'

SEQ ID No. 54: CAT192HC + GGGGS (TVTVSGGGGSSAS), Forward
5'-caccaccgtgacagtgtctggcggcggcggcagcagcgccagca-3'

SEQ ID No. 55: CAT192HC + GGGGS (TVTVSGGGGSSAS), Complement
5'-tgctggcgctgctgccgccgccgccagacactgtcacggtggtg-3'

SEQ ID No. 56: Mutant Heavy Chain with 1 Additional Amino Acid Inserted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGSASTKGPSVFPLAPSSKSTSGGTAALGCLVKD

YFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISR

TPEVTCVVVDVSHEDPEVKFNVVYVDGVEVHNAKTKPREEQYNSTYRVVSVL

TVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTV

DKSRWQQGNVFSCSVMHEALHNHYTQKSLSLSPGK

SEQ ID No. 57: Mutant Heavy Chain with 2 Additional Amino Acids Inserted
and 2 Amino Acids Deleted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGGSAKGPSVFPLAPSSKSTSGGTAALGCLVKDY

FPEPVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTV

DKSRWQQGNVFSCSVMHEALHNHYTQKSLSLSPGK

SEQ ID No. 58: Mutant Heavy Chain with 5 Additional Amino Acids Inserted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGGGGSSASTKGPSVFPLAPSSKSTSGGTAALGC

LVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDT
```

-continued

LMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID No. 59: CAT192HC + GG (TVTVSGGSAS), Forward
5'- caccaccgtgacagtgtctggcggcagcgccagca-3'

SEQ ID No. 60: CAT192HC + GG (TVTVSGGSAS), Complement
5'- tgctggcgctgccgccagacactgtcacggtggtg-3'

SEQ ID No. 61: Mutant Heavy Chain with 2 Additional Amino Acids Inserted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGGSASTKGPSVFPLAPSSKSTSGGTAALGCLVK

DYFPEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSKLT

VDKSRWQQGNVFSCSVMHEALHNHYTQKSLSLSPGK

SEQ ID No. 62: GGGS

SEQ ID No. 63: GGGGS

---

The invention claimed is:

1. A method of treating a bone remodeling disease in a human in need thereof, comprising administering an isolated binding protein that binds TGFβ1, or a TGFβ1-binding fragment thereof, wherein the isolated binding protein comprises (i) an immunoglobulin heavy chain (HC) having a variable domain (VH) amino acid sequence set forth in SEQ ID NO: 1, and (ii) an immunoglobulin light chain (LC) having a variable domain (VL) amino acid sequence set forth in SEQ ID NO: 3, wherein
   (a) the HC comprises an elbow region comprising a first linker, or
   (b) the LC comprises an elbow region comprising a second linker, or
   (c) both (a) and (b),
wherein the first and second linkers independently are one to five amino acids in length and comprise G, GG, GGS, GGGS (SEQ ID NO: 62), or GGGGS (SEQ ID NO: 63).

2. The method of claim 1, wherein the HC is of a human IgG4 isotype.

3. The method of claim 2, wherein the HC comprises a hinge region comprising an S228P mutation (Eu numbering).

4. The method of claim 1, wherein the HC is of a human IgG1 isotype.

5. The method of claim 1, wherein the HC comprises SEQ ID NO: 56, 57, 58, or 61.

6. The method of claim 5, wherein the LC comprises any one of SEQ ID NOs: 16 and 38-43.

7. The method of claim 1, wherein the LC comprises any one of SEQ ID NOs: 39-43.

8. The method of claim 7, wherein the HC comprises any one of SEQ ID NOs: 17, 18, 56-58, and 61.

9. A method of treating a bone remodeling disease in a human in need thereof, comprising administering an isolated binding protein that binds TGFβ1, or a TGFβ1-binding fragment thereof, wherein the isolated binding protein comprises an immunoglobulin heavy chain and an immunoglobulin light chain comprising:

SEQ ID NOs: 18 and 39, respectively;
SEQ ID NOs: 18 and 40, respectively;
SEQ ID NOs: 18 and 41, respectively;
SEQ ID NOs: 18 and 42, respectively;
SEQ ID NOs: 18 and 43, respectively;
SEQ ID NOs: 56 and 16, respectively;
SEQ ID NOs: 56 and 38, respectively;
SEQ ID NOs: 56 and 39, respectively;
SEQ ID NOs: 56 and 40, respectively;
SEQ ID NOs: 56 and 41, respectively;
SEQ ID NOs: 56 and 42, respectively;
SEQ ID NOs: 56 and 43, respectively;
SEQ ID NOs: 57 and 16, respectively;
SEQ ID NOs: 57 and 38, respectively;
SEQ ID NOs: 57 and 39, respectively;
SEQ ID NOs: 57 and 40, respectively;
SEQ ID NOs: 57 and 41, respectively;
SEQ ID NOs: 57 and 42, respectively;
SEQ ID NOs: 57 and 43, respectively;
SEQ ID NOs: 58 and 16, respectively;
SEQ ID NOs: 58 and 38, respectively;
SEQ ID NOs: 58 and 39, respectively;
SEQ ID NOs: 58 and 40, respectively;
SEQ ID NOs: 58 and 41, respectively;
SEQ ID NOs: 58 and 42, respectively;
SEQ ID NOs: 58 and 43, respectively;
SEQ ID NOs: 61 and 16, respectively;
SEQ ID NOs: 61 and 38, respectively;
SEQ ID NOs: 61 and 39, respectively;
SEQ ID NOs: 61 and 40, respectively;
SEQ ID NOs: 61 and 41, respectively;
SEQ ID NOs: 61 and 42, respectively; or
SEQ ID NOs: 61 and 43, respectively.

* * * * *

```
                         SEQUENCE LISTING

Sequence total quantity: 64
SEQ ID NO: 1            moltype = AA  length = 123
FEATURE                 Location/Qualifiers
source                  1..123
                        mol_type = protein
                        organism = Homo sapiens
SEQUENCE: 1
EVQLVESGGG VVQPGRSLRL SCAASGFTFS SYGMHWVRQA PGKELEWVAV ISYDGSIKYY   60
ADSVKGRFTI SRDNSKNTLY LQMNSLRAED TAVYYCARTG EYSGYDTDPQ YSWGQGTTVT  120
VSS                                                                123

SEQ ID NO: 2            moltype = AA  length = 123
FEATURE                 Location/Qualifiers
source                  1..123
                        mol_type = protein
                        organism = Homo sapiens
SEQUENCE: 2
QVQLVESGGG VVQPGRSLRL SCAASGFTFS SYGMHWVRQA PGKELEWVAV ISYDGSIKYY   60
ADSVKGRFTI SRDNSKNTLY LQMNSLRAED TAVYYCARTG EYSGYDTPAS PDWGQGTTVT  120
VSS                                                                123

SEQ ID NO: 3            moltype = AA  length = 107
FEATURE                 Location/Qualifiers
source                  1..107
                        mol_type = protein
                        organism = Homo sapiens
SEQUENCE: 3
EIVLTQSPSS LSASVGDRVT ITCRASQGIG DDLGWYQQKP GKAPILLIYG TSTLQSGVPS   60
RFSGSGSGTD FTLTINSLQP EDFATYYCLQ DSNYPLTFGG GTRLEIK                107

SEQ ID NO: 4            moltype = AA  length = 107
FEATURE                 Location/Qualifiers
source                  1..107
                        mol_type = protein
                        organism = Homo sapiens
SEQUENCE: 4
EIVLTQSPSS LSASVGDRVT ITCRSSQGIG DDLGWYQQKP GKAPILLIYG TSTLQSGVPS   60
```

```
RFSGSGSGTD FTLTINSLQP EDFATYYCLQ DSNYPLTFGG GTRLEIK                  107

SEQ ID NO: 5            moltype = AA   length = 22
FEATURE                 Location/Qualifiers
source                  1..22
                        mol_type = protein
                        organism = Homo sapiens
SEQUENCE: 5
PKSCDKTHTC PPCPAPELLG GP                                             22

SEQ ID NO: 6            moltype = AA   length = 209
FEATURE                 Location/Qualifiers
source                  1..209
                        mol_type = protein
                        organism = Homo sapiens
SEQUENCE: 6
SVFLFPPKPK DTLMISRTPE VTCVVVDVSH EDPEVKFNWY VDGVEVHNAK TKPREEQYNS     60
TYRVVSVLTV LHQDWLNGKE YKCKVSNKAL PAPIEKTISK AKGQPREPQV YTLPPSRDEL    120
TKNQVSLTCL VKGFYPSDIA VEWESNGQPE NNYKTTPPVL DSDGSFFLYS KLTVDKSRWQ    180
QGNVFSCSVM HEALHNHYTQ KSLSLSPGK                                     209

SEQ ID NO: 7            moltype = AA   length = 5
FEATURE                 Location/Qualifiers
source                  1..5
                        mol_type = protein
                        organism = Homo sapiens
SEQUENCE: 7
SYGMH                                                                 5

SEQ ID NO: 8            moltype = AA   length = 17
FEATURE                 Location/Qualifiers
source                  1..17
                        mol_type = protein
                        organism = Homo sapiens
SEQUENCE: 8
VISYDGSIKY YADSVKG                                                   17

SEQ ID NO: 9            moltype = AA   length = 14
FEATURE                 Location/Qualifiers
source                  1..14
                        mol_type = protein
                        organism = Homo sapiens
SEQUENCE: 9
TGEYSGYDTS GVEL                                                      14

SEQ ID NO: 10           moltype = AA   length = 14
FEATURE                 Location/Qualifiers
source                  1..14
                        mol_type = protein
                        organism = Homo sapiens
SEQUENCE: 10
TGEYSGYDTD PQYS                                                      14

SEQ ID NO: 11           moltype = AA   length = 14
FEATURE                 Location/Qualifiers
source                  1..14
                        mol_type = protein
                        organism = Homo sapiens
SEQUENCE: 11
TGFYSGYDTP ASPD                                                      14

SEQ ID NO: 12           moltype = AA   length = 11
FEATURE                 Location/Qualifiers
source                  1..11
                        mol_type = protein
                        organism = Homo sapiens
SEQUENCE: 12
RASQGIGDDL G                                                         11

SEQ ID NO: 13           moltype = AA   length = 7
FEATURE                 Location/Qualifiers
source                  1..7
                        mol_type = protein
                        organism = Homo sapiens
SEQUENCE: 13
GTSTLQS                                                               7

SEQ ID NO: 14           moltype = AA   length = 9
FEATURE                 Location/Qualifiers
```

```
source                    1..9
                          mol_type = protein
                          organism = Homo sapiens
SEQUENCE: 14
LQDSNYPLT                                                                    9

SEQ ID NO: 15             moltype = AA  length = 14
FEATURE                   Location/Qualifiers
VARIANT                   3
                          note = Any amino acid
VARIANT                   10..14
                          note = Any amino acid
source                    1..14
                          mol_type = protein
                          organism = Homo sapiens
SEQUENCE: 15
TGXYSGYDTX XXXX                                                             14

SEQ ID NO: 16             moltype = AA  length = 213
FEATURE                   Location/Qualifiers
source                    1..213
                          mol_type = protein
                          organism = Homo sapiens
SEQUENCE: 16
EWLTQSPSSL SASVGDRVTI TCRASQGIGD DLGWYQQKPG KAPILLIYGT STLQSGVPSR            60
FSGSGSGTDF TLTINSLQPE DFATYYCLQD SNYPLTFGGG TRLEIKRTVA APSVFIFPPS           120
DEQLKSGTAS VVCLLNNFYP REAKVQWKVD NALQSGNSQE SVTEQDSKDS TYSLSSTLTL           180
SKADYEKHKV YACEVTHQGL SSPVTKSFNR GEC                                        213

SEQ ID NO: 17             moltype = AA  length = 450
FEATURE                   Location/Qualifiers
source                    1..450
                          mol_type = protein
                          organism = Homo sapiens
SEQUENCE: 17
EVQLVESGGG VVQPGRSLRL SCAASGFTFS SYGMHWVRQA PGKELEWVAV ISYDGSIKYY            60
ADSVKGRFTI SRDNSKNTLY LQMNSLRAED TAVYYCARTG EYSGYDTDPQ YSWGQGTTVT           120
VSSASTKGPS VFPLAPCSRS TSESTAALGC LVKDYFPEPV TVSWNSGALT SGVHTFPAVL           180
QSSGLYSLSS VVTVPSSSLG TKTYTCNVDH KPSNTKVDKR VESKYGPPCP SCPAPEFLGG           240
PSVFLFPPKP KDTLMISRTP EVTCVVVDVS QEDPEVQFNW YVDGVEVHNA KTKPREEQFN           300
STYRVVSVLT VLHQDWLNGK EYKCKVSNKG LPSSIEKTIS KAKGQPREPQ VYTLPPSQEE           360
MTKNQVSLTC LVKGFYPSDI AVEWESNGQP ENNYKTTPPV LDSDGSFFLY SRLTVDKSRW           420
QEGNVFSCSV MHEALHNHYT QKSLSLSLGK                                            450

SEQ ID NO: 18             moltype = AA  length = 450
FEATURE                   Location/Qualifiers
source                    1..450
                          mol_type = protein
                          organism = Homo sapiens
SEQUENCE: 18
EVQLVESGGG VVQPGRSLRL SCAASGFTFS SYGMHWVRQA PGKELEWVAV ISYDGSIKYY            60
ADSVKGRFTI SRDNSKNTLY LQMNSLRAED TAVYYCARTG EYSGYDTDPQ YSWGQGTTVT           120
VSSASTKGPS VFPLAPCSRS TSESTAALGC LVKDYFPEPV TVSWNSGALT SGVHTFPAVL           180
QSSGLYSLSS VVTVPSSSLG TKTYTCNVDH KPSNTKVDKR VESKYGPPCP PCPAPEFLGG           240
PSVFLFPPKP KDTLMISRTP EVTCVVVDVS QEDPEVQFNW YVDGVEVHNA KTKPREEQFN           300
STYRVVSVLT VLHQDWLNGK EYKCKVSNKG LPSSIEKTIS KAKGQPREPQ VYTLPPSQEE           360
MTKNQVSLTC LVKGFYPSDI AVEWESNGQP ENNYKTTPPV LDSDGSFFLY SRLTVDKSRW           420
QEGNVFSCSV MHEALHNHYT QKSLSLSLGK                                            450

SEQ ID NO: 19             moltype = AA  length = 245
FEATURE                   Location/Qualifiers
source                    1..245
                          mol_type = protein
                          organism = Homo sapiens
SEQUENCE: 19
EVQLVESGGG VVQPGRSLRL SCAASGFTFS SYGMHWVRQA PGKELEWVAV ISYDGSIKYY            60
ADSVKGRFTI SRDNSKNTLY LQMNSLRAED TAVYYCARTG EYSGYDTDPQ YSWGQGTTVT           120
VSSGGGGSGG GGSGGGGSEI VLTQSPSSLS ASVGDRVTIT CRSSQGIGDD LGWYQQKPGK           180
APILLIYGTS TLQSGVPSRF SGSGSGTDFT LTINSLQPED FATYYCLQDS NYPLTFGGGT           240
RLEIK                                                                       245

SEQ ID NO: 20             moltype = AA  length = 112
FEATURE                   Location/Qualifiers
source                    1..112
                          mol_type = protein
                          organism = Homo sapiens
SEQUENCE: 20
ALDTNYCFSS TEKNCCVRQL YIDFRKDLGW KWIHEPKGYH ANFCLGPCPY IWSLDTQYSK            60
VLALYNQHNP GASAAPCCVP QALEPLPIVY YVGRKPKVEQ LSNMIVRSCK CS                   112
```

```
SEQ ID NO: 21            moltype = AA  length = 8
FEATURE                  Location/Qualifiers
source                   1..8
                         mol_type = protein
                         organism = Homo sapiens
SEQUENCE: 21
LEIKRTVA                                                                  8

SEQ ID NO: 22            moltype = AA  length = 9
FEATURE                  Location/Qualifiers
source                   1..9
                         mol_type = protein
                         organism = Homo sapiens
SEQUENCE: 22
LEIKGRTVA                                                                 9

SEQ ID NO: 23            moltype = AA  length = 10
FEATURE                  Location/Qualifiers
source                   1..10
                         mol_type = protein
                         organism = Homo sapiens
SEQUENCE: 23
LEIKGGRTVA                                                               10

SEQ ID NO: 24            moltype = AA  length = 11
FEATURE                  Location/Qualifiers
source                   1..11
                         mol_type = protein
                         organism = Homo sapiens
SEQUENCE: 24
LEIKGGSRTV A                                                             11

SEQ ID NO: 25            moltype = AA  length = 12
FEATURE                  Location/Qualifiers
source                   1..12
                         mol_type = protein
                         organism = Homo sapiens
SEQUENCE: 25
LEIKGGGSRT VA                                                            12

SEQ ID NO: 26            moltype = AA  length = 13
FEATURE                  Location/Qualifiers
source                   1..13
                         mol_type = protein
                         organism = Homo sapiens
SEQUENCE: 26
LEIKGGGGSR TVA                                                           13

SEQ ID NO: 27            moltype = DNA  length = 702
FEATURE                  Location/Qualifiers
source                   1..702
                         mol_type = genomic DNA
                         organism = Homo sapiens
SEQUENCE: 27
atgggctggt cctgcatcat cctgtttctg gtggccacag ccaccggcgt gcacagcgag         60
atcgtgctga cacagagccc cagcagcctg tctgccagcg tgggcgacag agtgaccatc        120
acctgtagag ccagccaggg catcggcgac gacctgggat ggtatcagca gaagcctggc        180
aaggccccca tcctgctgat ctacggcacc agcacactgc agagcggcgt gccctccaga        240
ttttctggca gcggctccgg caccgacttc accctgacca tcaacagcct gcagcccgag        300
gacttcgcca cctactactg tctgcaagac agcaactacc ccctgacctt cggcggaggc        360
acccggctga aaatcaagcg tacggtggcc gctccttccg tgttcatctt ccctcccctc        420
gacgagcagc tgaagtccgg caccgcctcc gtggtgtgtc tgctgaacaa cttctaccct        480
cgggaggcca aggtgcagtg gaaggtggac aacgccctgc agtccggcaa ctcccaggag        540
tccgtcaccg agcaggactc caaggacagc acctactccc tgtcctccac cctgaccctg        600
tccaaggccg actacgagaa gcacaaggtg tacgcctgtg aggtgaccca ccagggcctg        660
tccagccctg tgaccaagtc cttcaaccgg ggcgagtgct ga                           702

SEQ ID NO: 28            moltype = DNA  length = 31
FEATURE                  Location/Qualifiers
source                   1..31
                         mol_type = genomic DNA
                         organism = Homo sapiens
SEQUENCE: 28
ggctggaaat caagggccgt acggtggccg c                                       31

SEQ ID NO: 29            moltype = DNA  length = 31
FEATURE                  Location/Qualifiers
source                   1..31
```

```
                        mol_type = genomic DNA
                        organism = Homo sapiens
SEQUENCE: 29
gcggccaccg tacggccctt gatttccagc c                              31

SEQ ID NO: 30           moltype = DNA  length = 34
FEATURE                 Location/Qualifiers
source                  1..34
                        mol_type = genomic DNA
                        organism = Homo sapiens
SEQUENCE: 30
ggctggaaat caagggcggc cgtacggtgg ccgc                           34

SEQ ID NO: 31           moltype = DNA  length = 34
FEATURE                 Location/Qualifiers
source                  1..34
                        mol_type = genomic DNA
                        organism = Homo sapiens
SEQUENCE: 31
gcggccaccg tacggccgcc cttgatttcc agcc                           34

SEQ ID NO: 32           moltype = DNA  length = 37
FEATURE                 Location/Qualifiers
source                  1..37
                        mol_type = genomic DNA
                        organism = Homo sapiens
SEQUENCE: 32
ggctggaaat caagggcggc agccgtacgg tggccgc                        37

SEQ ID NO: 33           moltype = DNA  length = 37
FEATURE                 Location/Qualifiers
source                  1..37
                        mol_type = genomic DNA
                        organism = Homo sapiens
SEQUENCE: 33
gcggccaccg tacggctgcc gcccttgatt tccagcc                        37

SEQ ID NO: 34           moltype = DNA  length = 40
FEATURE                 Location/Qualifiers
source                  1..40
                        mol_type = genomic DNA
                        organism = Homo sapiens
SEQUENCE: 34
ggctggaaat caagggcggc ggcagccgta cggtggccgc                     40

SEQ ID NO: 35           moltype = DNA  length = 40
FEATURE                 Location/Qualifiers
source                  1..40
                        mol_type = genomic DNA
                        organism = Homo sapiens
SEQUENCE: 35
gcggccaccg tacggctgcc gccgcccttg atttccagcc                     40

SEQ ID NO: 36           moltype = DNA  length = 43
FEATURE                 Location/Qualifiers
source                  1..43
                        mol_type = genomic DNA
                        organism = Homo sapiens
SEQUENCE: 36
ggctggaaat caagggcggc ggcggcagcc gtacggtggc cgc                 43

SEQ ID NO: 37           moltype = DNA  length = 43
FEATURE                 Location/Qualifiers
source                  1..43
                        mol_type = genomic DNA
                        organism = Homo sapiens
SEQUENCE: 37
gcggccaccg tacggctgcc gccgccgccc ttgatttcca gcc                 43

SEQ ID NO: 38           moltype = AA   length = 214
FEATURE                 Location/Qualifiers
source                  1..214
                        mol_type = protein
                        organism = Homo sapiens
SEQUENCE: 38
EIVLTQSPSS LSASVGDRVT ITCRASQGIG DDLGWYQQKP GKAPILLIYG TSTLQSGVPS  60
RFSGSGSGTD FTLTINSLQP EDFATYYCLQ DSNYPLTFGG GTRLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                           214
```

```
SEQ ID NO: 39           moltype = AA   length = 215
FEATURE                 Location/Qualifiers
source                  1..215
                        mol_type = protein
                        organism = Homo sapiens
SEQUENCE: 39
EIVLTQSPSS LSASVGDRVT ITCRASQGIG DDLGWYQQKP GKAPILLIYG TSTLQSGVPS      60
RFSGSGSGTD FTLTINSLQP EDFATYYCLQ DSNYPLTFGG GTRLEIKGRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 40           moltype = AA   length = 216
FEATURE                 Location/Qualifiers
source                  1..216
                        mol_type = protein
                        organism = Homo sapiens
SEQUENCE: 40
EIVLTQSPSS LSASVGDRVT ITCRASQGIG DDLGWYQQKP GKAPILLIYG TSTLQSGVPS      60
RFSGSGSGTD FTLTINSLQP EDFATYYCLQ DSNYPLTFGG GTRLEIKGGR TVAAPSVFIF     120
PPSDEQLKSG TASVVCLLNN FYPREAKVQW KVDNALQSGN SQESVTEQDS KDSTYSLSST     180
LTLSKADYEK HKVYACEVTH QGLSSPVTKS FNRGEC                               216

SEQ ID NO: 41           moltype = AA   length = 217
FEATURE                 Location/Qualifiers
source                  1..217
                        mol_type = protein
                        organism = Homo sapiens
SEQUENCE: 41
EIVLTQSPSS LSASVGDRVT ITCRASQGIG DDLGWYQQKP GKAPILLIYG TSTLQSGVPS      60
RFSGSGSGTD FTLTINSLQP EDFATYYCLQ DSNYPLTFGG GTRLEIKGGS RTVAAPSVFI     120
FPPSDEQLKS GTASVVCLLN NFYPREAKVQ WKVDNALQSG NSQESVTEQD SKDSTYSLSS     180
TLTLSKADYE KHKVYACEVT HQGLSSPVTK SFNRGEC                              217

SEQ ID NO: 42           moltype = AA   length = 218
FEATURE                 Location/Qualifiers
source                  1..218
                        mol_type = protein
                        organism = Homo sapiens
SEQUENCE: 42
EIVLTQSPSS LSASVGDRVT ITCRASQGIG DDLGWYQQKP GKAPILLIYG TSTLQSGVPS      60
RFSGSGSGTD FTLTINSLQP EDFATYYCLQ DSNYPLTFGG GTRLEIKGGG SRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 43           moltype = AA   length = 219
FEATURE                 Location/Qualifiers
source                  1..219
                        mol_type = protein
                        organism = Homo sapiens
SEQUENCE: 43
EIVLTQSPSS LSASVGDRVT ITCRASQGIG DDLGWYQQKP GKAPILLIYG TSTLQSGVPS      60
RFSGSGSGTD FTLTINSLQP EDFATYYCLQ DSNYPLTFGG GTRLEIKGGG GSRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 44           moltype = AA   length = 8
FEATURE                 Location/Qualifiers
source                  1..8
                        mol_type = protein
                        organism = Homo sapiens
SEQUENCE: 44
TVTVSSAS                                                               8

SEQ ID NO: 45           moltype = AA   length = 9
FEATURE                 Location/Qualifiers
source                  1..9
                        mol_type = protein
                        organism = Homo sapiens
SEQUENCE: 45
TVTVSGSAS                                                              9

SEQ ID NO: 46           moltype = AA   length = 10
FEATURE                 Location/Qualifiers
source                  1..10
                        mol_type = protein
                        organism = Homo sapiens
SEQUENCE: 46
TVTVSGGSAS                                                            10
```

```
SEQ ID NO: 47            moltype = AA  length = 9
FEATURE                  Location/Qualifiers
source                   1..9
                         mol_type = protein
                         organism = Homo sapiens
SEQUENCE: 47
TVTVSGGSA                                                              9

SEQ ID NO: 48            moltype = AA  length = 13
FEATURE                  Location/Qualifiers
source                   1..13
                         mol_type = protein
                         organism = Homo sapiens
SEQUENCE: 48
TVTVSGGGGS SAS                                                        13

SEQ ID NO: 49            moltype = DNA  length = 738
FEATURE                  Location/Qualifiers
source                   1..738
                         mol_type = genomic DNA
                         organism = Homo sapiens
SEQUENCE: 49
atgggctggt cctgcatcat cctgtttctg gtggccaccg ccaccggcgt gcactctgaa     60
gtgcagctgt tggaatctgg cggcggagtg gtgcagcctg gcagaagcct gagactgagc   120
tgtgccgcca gcggcttcac cttcagcagc tacggaatgc actgggtgcg ccaggcccct   180
ggcaaagaac tggaatgggt ggccgtgatc agctacgacg gcagcatcaa gtactacgcc   240
gacagcgtga agggccggtt caccatctcc cgggacaaca gcaagaacac cctgtacctg   300
cagatgaaca gcctgcgggc cgaggacacc gccgtgtact actgtgctag aaccggcgag   360
tacagcggct acgacaccga ccctcagtac tcttggggcc agggcaccac cgtgacagtg   420
tctagcgcca gcaccaaggg cccaagcgtg ttccctctgg ccccttgcag cagaagcacc   480
agcgaatcta cagccgccct gggctgcctc gtgaaggact actttcccga gcccgtgaca   540
gtgtcctgga actctggcgc cctgaccagc ggagtgcata ccttccagc cgtgctgcag   600
agcagcggcc tgtactctct gagcagcgtc gtgactgtgc ccagcagctc tctgggcacc   660
aagacctaca cctgtaacgt ggaccacaag cccagcaaca ccaaggtgga caagagagtg   720
catcaccacc accatcac                                                738

SEQ ID NO: 50            moltype = DNA  length = 29
FEATURE                  Location/Qualifiers
source                   1..29
                         mol_type = genomic DNA
                         organism = Homo sapiens
SEQUENCE: 50
ccaccgtgac agtgtctggc agcgccagc                                       29

SEQ ID NO: 51            moltype = DNA  length = 29
FEATURE                  Location/Qualifiers
source                   1..29
                         mol_type = genomic DNA
                         organism = Homo sapiens
SEQUENCE: 51
gctggcgctg ccagacactg tcacggtgg                                       29

SEQ ID NO: 52            moltype = DNA  length = 32
FEATURE                  Location/Qualifiers
source                   1..32
                         mol_type = genomic DNA
                         organism = Homo sapiens
SEQUENCE: 52
ccaccgtgac agtgtctggc ggcagcgcca gc                                   32

SEQ ID NO: 53            moltype = DNA  length = 32
FEATURE                  Location/Qualifiers
source                   1..32
                         mol_type = genomic DNA
                         organism = Homo sapiens
SEQUENCE: 53
gctggcgctg ccgccagaca ctgtcacggt gg                                   32

SEQ ID NO: 54            moltype = DNA  length = 44
FEATURE                  Location/Qualifiers
source                   1..44
                         mol_type = genomic DNA
                         organism = Homo sapiens
SEQUENCE: 54
caccaccgtg acagtgtctg gcggcggcgg cagcagcgcc agca                       44

SEQ ID NO: 55            moltype = DNA  length = 44
FEATURE                  Location/Qualifiers
```

```
                        source               1..44
                                             mol_type = genomic DNA
                                             organism = Homo sapiens
SEQUENCE: 55
tgctggcgct gctgccgccg ccgccagaca ctgtcacggt ggtg                             44

SEQ ID NO: 56           moltype = AA   length = 454
FEATURE                 Location/Qualifiers
source                  1..454
                        mol_type = protein
                        organism = Homo sapiens
SEQUENCE: 56
EVQLVESGGG VVQPGRSLRL SCAASGFTFS SYGMHWVRQA PGKELEWVAV ISYDGSIKYY              60
ADSVKGRFTI SRDNSKNTLY LQMNSLRAED TAVYYCARTG EYSGYDTDPQ YSWGQGTTVT             120
VSGGSASTKGP SVFPLAPSSK STSGGTAALG CLVKDYFPEP VTVSWNSGAL TSGVHTFPAV            180
LQSSGLYSLS SVVTVPSSSL GTQTYICNVN HKPSNTKVDK KVEPKSCDKT HTCPPCPAPE             240
LLGGPSVFLF PPKPKDTLMI SRTPEVTCVV VDVSHEDPEV KFNWYVDGVE VHNAKTKPRE             300
EQYNSTYRVV SVLTVLHQDW LNGKEYKCKV SNKALPAPIE KTISKAKGQP REPQVYTLPP             360
SRDELTKNQV SLTCLVKGFY PSDIAVEWES NGQPENNYKT TPPVLDSDGS FFLYSKLTVD             420
KSRWQQGNVF SCSVMHEALH NHYTQKSLSL SPGK                                        454

SEQ ID NO: 57           moltype = AA   length = 453
FEATURE                 Location/Qualifiers
source                  1..453
                        mol_type = protein
                        organism = Homo sapiens
SEQUENCE: 57
EVQLVESGGG VVQPGRSLRL SCAASGFTFS SYGMHWVRQA PGKELEWVAV ISYDGSIKYY              60
ADSVKGRFTI SRDNSKNTLY LQMNSLRAED TAVYYCARTG EYSGYDTDPQ YSWGQGTTVT             120
VSGGSASTKGP VFPLAPSSKS TSGGTAALGC LVKDYFPEPV TVSWNSGALT SGVHTFPAVL            180
QSSGLYSLSS VVTVPSSSLG TQTYICNVNH KPSNTKVDKK VEPKSCDKTH TCPPCPAPEL             240
LGGPSVFLFP PKPKDTLMIS RTPEVTCVVV DVSHEDPEVK FNWYVDGVEV HNAKTKPREE             300
QYNSTYRVVS VLTVLHQDWL NGKEYKCKVS NKALPAPIEK TISKAKGQPR EPQVYTLPPS             360
RDELTKNQVS LTCLVKGFYP SDIAVEWESN GQPENNYKTT PPVLDSDGSF FLYSKLTVDK             420
SRWQQGNVFS CSVMHEALHN HYTQKSLSLS PGK                                         453

SEQ ID NO: 58           moltype = AA   length = 458
FEATURE                 Location/Qualifiers
source                  1..458
                        mol_type = protein
                        organism = Homo sapiens
SEQUENCE: 58
EVQLVESGGG VVQPGRSLRL SCAASGFTFS SYGMHWVRQA PGKELEWVAV ISYDGSIKYY              60
ADSVKGRFTI SRDNSKNTLY LQMNSLRAED TAVYYCARTG EYSGYDTDPQ YSWGQGTTVT             120
VSGGGGSSAS TKGPSVFPLA PSSKSTSGGT AALGCLVKDY FPEPVTVSWN SGALTSGVHT             180
FPAVLQSSGL YSLSSVVTVP SSSLGTQTYI CNVNHKPSNT KVDKKVEPKS CDKTHTCPPC             240
PAPELLGGPS VFLFPPKPKD TLMISRTPEV TCVVVDVSHE DPEVKFNWYV DGVEVHNAKT             300
KPREEQYNST YRVVSVLTVL HQDWLNGKEY KCKVSNKALP APIEKTISKA KGQPREPQVY             360
TLPPSRDELT KNQVSLTCLV KGFYPSDIAV EWESNGQPEN NYKTTPPVLD SDGSFFLYSK             420
LTVDKSRWQQ GNVFSCSVMH EALHNHYTQK SLSLSPGK                                    458

SEQ ID NO: 59           moltype = DNA   length = 35
FEATURE                 Location/Qualifiers
source                  1..35
                        mol_type = genomic DNA
                        organism = Homo sapiens
SEQUENCE: 59
caccaccgtg acagtgtctg gcggcagcgc cagca                                       35

SEQ ID NO: 60           moltype = DNA   length = 35
FEATURE                 Location/Qualifiers
source                  1..35
                        mol_type = genomic DNA
                        organism = Homo sapiens
SEQUENCE: 60
tgctggcgct gccgccagac actgtcacgg tggtg                                       35

SEQ ID NO: 61           moltype = AA   length = 455
FEATURE                 Location/Qualifiers
source                  1..455
                        mol_type = protein
                        organism = Homo sapiens
SEQUENCE: 61
EVQLVESGGG VVQPGRSLRL SCAASGFTFS SYGMHWVRQA PGKELEWVAV ISYDGSIKYY              60
ADSVKGRFTI SRDNSKNTLY LQMNSLRAED TAVYYCARTG EYSGYDTDPQ YSWGQGTTVT             120
VSGGSASTKG PSVFPLAPSS KSTSGGTAAL GCLVKDYFPE PVTVSWNSGA LTSGVHTFPA             180
VLQSSGLYSL SSVVTVPSSS LGTQTYICNV NHKPSNTKVD KKVEPKSCDK THTCPPCPAP             240
ELLGGPSVFL FPPKPKDTLM ISRTPEVTCV VVDVSHEDPE VKFNWYVDGV EVHNAKTKPR             300
EEQYNSTYRV SVLTVLHQD WLNGKEYKCK VSNKALPAPI EKTISKAKGQ PREPQVYTLP              360
```

```
PSRDELTKNQ VSLTCLVKGF YPSDIAVEWE SNGQPENNYK TTPPVLDSDG SFFLYSKLTV     420
DKSRWQQGNV FSCSVMHEAL HNHYTQKSLS LSPGK                                455

SEQ ID NO: 62           moltype = AA  length = 4
FEATURE                 Location/Qualifiers
REGION                  1..4
                        note = Description of Artificial Sequence: Synthetic linker
source                  1..4
                        mol_type = protein
                        organism = synthetic construct
SEQUENCE: 62
GGGS                                                                    4

SEQ ID NO: 63           moltype = AA  length = 5
FEATURE                 Location/Qualifiers
REGION                  1..5
                        note = Description of Artificial Sequence: Synthetic linker
source                  1..5
                        mol_type = protein
                        organism = synthetic construct
SEQUENCE: 63
GGGGS                                                                   5

SEQ ID NO: 64           moltype = AA  length = 15
FEATURE                 Location/Qualifiers
REGION                  1..15
                        note = Description of Artificial Sequence: Synthetic linker
source                  1..15
                        mol_type = protein
                        organism = synthetic construct
SEQUENCE: 64
GGGGSGGGGS GGGGS                                                       15
```